US005807863A

United States Patent [19]

Eberle et al.

[11] Patent Number: 5,807,863

[45] Date of Patent: Sep. 15, 1998

[54] 2-(4-PYRAZOLYLOXY-PYRIMIDIN-5-YL) ACETIC ACID DERIVATIVES

[75] Inventors: Martin Eberle, Bottmingen, Switzerland; Clemens Lamberth, Rümmingen, Germany; Fritz Schaub, Aesch, Switzerland

[73] Assignee: Novartis Corporation, Summit, N.J.

[21] Appl. No.: 715,980

[22] Filed: Sep. 19, 1996

[30] Foreign Application Priority Data

Sep. 28, 1995 [GB] United Kingdom ................ 9519787.7

[51] Int. Cl.[6] ...................... C07D 401/14; C07D 403/12; A01N 43/54

[52] U.S. Cl. .......................... 514/269; 544/300; 544/310; 544/319; 544/320; 544/321; 544/296; 544/230; 544/284; 514/259; 514/252; 514/272; 514/274

[58] Field of Search .................................... 544/300, 310, 544/316, 317, 319, 320, 321, 296, 238, 284; 514/269, 272, 274, 252, 259

[56] References Cited

U.S. PATENT DOCUMENTS 5,474,996 12/1995 Caille et al. ............................ 514/256

FOREIGN PATENT DOCUMENTS

| | | |
|---|---|---|
| A 243012 | 10/1987 | European Pat. Off. . |
| A 299694 | 1/1989 | European Pat. Off. . |
| A 383117 | 8/1990 | European Pat. Off. . |
| 515265 | 5/1991 | European Pat. Off. . |
| A 471261 | 2/1992 | European Pat. Off. . |
| A 503436 | 9/1992 | European Pat. Off. . |
| A 581095 | 2/1994 | European Pat. Off. . |
| A 634405 | 1/1995 | European Pat. Off. . |
| A 667343 | 8/1995 | European Pat. Off. . |
| 248143 | 7/1993 | New Zealand . |
| 2 193 495 | 2/1988 | United Kingdom . |
| WO 95/05368 | 2/1995 | WIPO . |

*Primary Examiner*—John M. Ford
*Attorney, Agent, or Firm*—Michael P. Morris

[57] ABSTRACT

This invention relates to novel 2-(4-pyrazolyloxy-pyrimidin-5-yl) acetic acid derivatives of formula I

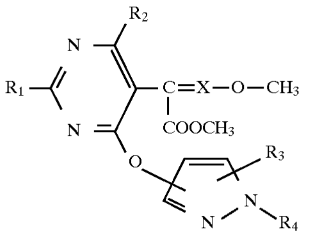

(I)

wherein $R_1$ is hydrogen, $C_{1-4}$alkyl, $C_{1-4}$alkoxy, $C_{1-4}$alkylthio, $C_{3-6}$cycloalkyl, or di-$C_{1-4}$alkylamino, $R_2$ is hydrogen, $C_{1-4}$alkyl, $C_{1-4}$alkoxy, $C_{1-4}$alkylthio, or di-$C_{1-4}$alkyl-amino, $R_3$ is hydrogen or methyl, $R_4$ is aryl, aryl-$C_{1-4}$alkyl, heteroaryl, or heteroaryl-$C_{1-4}$alkyl, wherein each of the aromatic rings may be optionally substituted; and X is CH or nitrogen;

the use of such compounds for the control of phytopathogens, compositions for facilitating such use, and the preparation of the compounds of formula I.

12 Claims, No Drawings

2-(4-PYRAZOLYLOXY-PYRIMIDIN-5-YL) ACETIC ACID DERIVATIVES

This invention relates to novel 2-(4-pyrazolyloxy-pyrimidin-5-yl) acetic acid derivatives, the synthesis thereof and the use of said compounds for the control of phytopathogens.

It has now been found that compounds of formula I

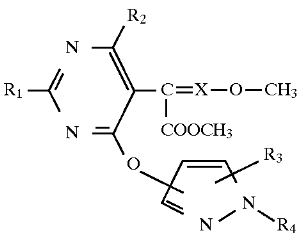

(I)

wherein $R_1$ is hydrogen, $C_{1-4}$alkyl, $C_{1-4}$alkoxy, $C_{1-4}$alkylthio, $C_{3-6}$cycloalkyl, or di-$C_{1-4}$alkylamino, $R_2$ is hydrogen, $C_{1-4}$alkyl, $C_{1-4}$alkoxy, $C_{1-4}$alkylthio, or di-$C_{1-4}$alkyl-amino, $R_3$ is hydrogen or methyl, $R_4$ is aryl, aryl-$C_{1-4}$alkyl, heteroaryl, or heteroaryl-$C_{1-4}$alkyl , wherein each of the aromatic rings may be optionally substituted; and X is CH or nitrogen;

are surprisingly effective against phytopathogens.

In the definitions of the radicals of formula I alkyl is understood to encompass straight-chain and branched alkyl groups. For example alkyl is methyl, ethyl, n-propyl, isopropyl, n-butyl, isobutyl, tertiary butyl or secondary butyl. Alkoxy for example encompasses methoxy, ethoxy, n-propoxy, isopropoxy, n-butyloxy, isobutyloxy, tertiary butyloxy or secondary butyloxy. Alkylthio designates methylthio, ethylthio, isopropylthio, propylthio, n-butylthio, isobutylthio, tertiary butylthio or secondary butylthio. Cycloalkyl designates for example cyclopropyl, cyclobutyl, cyclopentyl or cyclohexyl. Dialkylamino designated for example dimethylamino, diethylamino, dipropylamino, ethylmethylamino, ethylpropylamino, methylbutylamino, methylpropylamino, or ethylbutylamino. Aryl stands for aromatic hydrocarbon radicals, for example phenyl or naphthyl, with phenyl being preferred. The aryl radical may optionally be further substituted. Heteroaryl stands for aromatic 5- or 5-membered cyclic radicals comprising one, two or three ring atoms selected from nitrogen, oxygen and sulfur, which may also be in condensed form with another heteroaryl radical or aryl radical. Heteroaryl is linked to the oxygen bridge through a ring member carbon atom. The heteroaryl may optionally be further substituted. Examples for heteroaryl are pyridyl, pyrimidinyl, thienyl, oxazolyl, oxadiazolyl, triazolyl, thiadiazolyl, furyl, isoxazolyl, thiazolyl, imidazolyl, pyridazinyl, quinolinyl, quinazolinyl, benzothienyl, benzofuryl, benzimidazolyl, pyrazolyl, benzothiazolyl, benzoxazolyl, and the like. Arylalkyl preferably designates phenylalkyl such as benzyl, phenylethyl, phenylpropyl, or 1-phenylethyl. The aryl radical may optionally be further substituted. Heteroarylalkyl designates an aromatic 5- or 6-membered cyclic radical comprising one, two or three ring atoms selected from nitrogen, oxygen and sulfur, being linked to the oxygen bridge through an alkylene group, like $—CH_2—$, $—CH_2—CH_2—$ or $—CH(CH_3)—$. The heteroaryl radical is linked to the alkylene group through a ring member carbon atom. Examples for heteroarylalkyl are thienylmethyl, thienylethyl, furylmethyl, pyridylmethyl, pyrrolylmethyl and the like. The pyrazolyl ring may be linked to the oxygen bridge via the 3- or 4-position. However, 3-pyrazolyl is preferred.

In radicals being combined from various other definitions, each of the definitions has the meanings given for the partial definition separately.

The above aryl and heteroaryl radicals may be further substituted. Where aryl or heteroaryl is substituted, it is preferably substituted by one, two or three radicals selected from the group comprising halogen, $C_{1-4}$alkyl, $C_{1-4}$alkoxy, $C_{1-4}$haloalkyl, $C_{1-4}$haloalkoxy, $C_{2-8}$acyl, benzoyl, $C_{1-4}$alkylthio, cyano, phenyl, phenoxy, nitro, or a group $—C(CH_3)═N—O—C_{1-4}$alkyl. Halogen designates fluorine, chlorine, bromine and iodine, with fluorine and chlorine being preferred. Haloalkyl designates straight chain or branched alkyl groups which are mono- to perhalogenated with straight-chain lower alkyl being the preferred alkyl and with fluorine perhalogenated with straight-chain lower alkyl being the preferred alkyl and with fluorine and chlorine being preferred halogens. Examples are trifluoromethyl, difluoromethyl, 2,2,2-trifluoroethyl or 2,2,3,3,3-pentafluoropropyl. Haloalkoxy designates alkoxy groups which are mono- to perhalogenated. Examples are difluoromethoxy, trifluoromethoxy, 2,2,2-trifluoroethoxy or 1,1,2,2-tetrafluoroethoxy. Examples for acyl are acetyl, propionyl, butyroyl, isopropionyl, hexanoyl or octanoyl.

Preferred subgroups of compounds of formula I or those wherein either a) $R_1$ is methyl, ethyl, or cyclopropyl; or b) $R_2$ is methyl or methoxy; or c) the pyrazole ring is linked to the oxygen bridge in 3- or 4-position; or d) $R_4$ is chlorophenyl, dichlorophenyl, fluorophenyl, methyl-chlorophenyl, trifluoromethylphenyl, trifluoromethyl-chlorophenyl, difluoromethoxyphenyl, trifluoromethoxyphenyl, methylphenyl, or dimethylphenyl.

A further preferred subgroup is wherein $R_1$ and $R_2$ are methyl, and $R_4$ is chlorophenyl, dichlorophenyl, fluorophenyl, methyl-chlorophenyl, trifluoromethylphenyl, trifluoromethyl-chlorophenyl, difluoromethoxyphenyl, trifluoromethoxyphenyl, methylphenyl, or dimethylphenyl.

Among this subgroup those compounds are preferred wherein X is CH.

Preferred individual compounds of formula I are:

methyl 2-[2,4-dimethyl-6-(1-(3-trifluoromethylphenyl)-1H)-pyrazol-3-yloxy)-pyrimidin-5-yl]-3-methoxyacrylate;

methyl 2-[2,4-dimethyl-6-(1-(3,5-dimethylphenyl)-1H-pyrazol-4-yloxy)-pyrimidin-5-yl]-3-methoxyacrylate;

methyl 2-[2,4-dimethyl-6-(1-(5-chloro-2-methylphenyl)-1H-pyrazol-3-yloxy)-pyrimidin-5yl]-3-methoxyacrylate; and methyl 2-[2-methyl-4-methoxy-6-(1-(5-chloro-2-methylphenyl)-1H-pyrazol-3-yloxy)-pyrimidin-5-yl]-3-methoxyacrylate.

The double bond of the acrylic acid structure in the compounds of formula I may be in E- or Z-form. In this document the E- and Z-forms are identified where meant specifically. In all other cases mixtures of the two isomers are intended. Where E- and Z-isomers are obtained during synthesis they may be separated by known techniques, such as crystallisation, chromatography or distillation. In the described methods of preparation preferably the E-forms are obtained.

Compounds of formula I may be obtained by O-methylation of a compound of formula II (II)

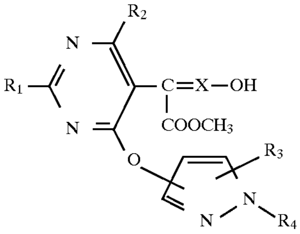

wherein $R_1$, $R_2$, $R_3$, $R_4$ and X are as defined above.

The O-methylation (II→I) can be carried out in a manner known per se for the preparation of 3-methoxyacrylates employing conventional methylation agents. Examples of suitable methylation agents include methyl iodide and dimethyl sulphate. The O-methylation is conveniently carried out in the presence of a base. The reaction temperature will conveniently lie in the range of from 0° C. to the boiling point of the reaction mixture, e.g. at about ambient temperature. Inert solvents may be used where desired. Examples of suitable bases include alkaline metal hydrides such as sodium hydride, alkaline metal alcoholates such as sodium methylate or alkaline metal carbonates. Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, alcohols such as methanol; acetone or a mixture comprising two or more of them. The desired end-product is isolated and purified according to known techniques, for example by evaporation of solvent, chromatography and crystallisation.

The compounds of formula I are only slightly basic in nature. They may form salts with sufficiently strong acids such as HCl and HBr.

The compounds of formula II wherein X is CH may be obtained by reaction of compounds of formula III (III)

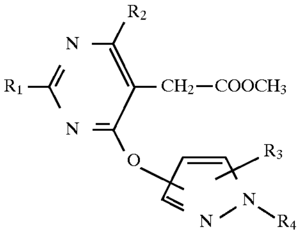

wherein $R_1$, $R_2$, $R_3$ and $R_4$ are as defined above and alkyl is $C_{1-10}$alkyl, with a formylating agent, e.g. N,N-diformylmethylamine, or methyl formate in the presence of a base.

This reaction is essentially a Claisen reaction and may be carried out under the conditions known for such reaction. The reaction (III→II) may be carried out in an inert solvent. Examples of suitable solvents are as described for the O-methylation of the compounds of formula II. Examples of suitable bases are such typically used for a Claisen reaction such as alkaline metal alcoholates, e.g. sodium methylate; alkaline metal hydrides, e.g. sodium hydride; and lithium amides or sodium amides, e.g. lithium diethylamide. The reaction temperature may vary within wide ranges, e.g. from 0° C. to the boiling point of the reaction mixture and is preferably at or near ambient temperature.

In an alternative process the compounds of formula II may also be obtained by reacting the compounds of formula III with a 1:1-adduct of dimethylformamide and dimethylsulfate in the presence of a strong base, such as t-BuOK and hydrolysing the obtained intermediate of formula IIIa (IIIa)

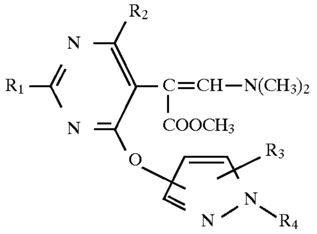

wherein $R_1$, $R_2$ and $R_3$ are as defined above.

This reaction variant is preferably carried out in an inert solvent at temperature between −70° C. to −30° C., preferably −60° C. to −40° C. Suitable solvents are ethers like tetrahydrofuran, dioxane, diethylether or glyme. Suitable bases are e.g. alkaline alcolates like t-BuOK; or alkaline hydrides like NaH, KH. The hydrolysing step is typically done in a two-phase system, by adding water, and at a temperature of 0° C. to +40° C., preferably at room temperature.

The compound of formula II wherein X is nitrogen may be obtained by reaction of compounds of formula III with an alkyl nitrite in the presence of a base, optionally in the presence of an inert solvent. In a variant of this process the compounds of formula II wherein X is N may also be obtained by reacting a compound of formula III with an alkyl nitrite in the presence of hydrochloric acid, optionally in an inert solvent. The reaction temperature will conveniently lie in the range of from −40° C. to +30° C. e.g. at about −20° C. to 0° C. Inert solvents may be used where desired. Examples of suitable bases include alkaline metal hydrides such as sodium hydride and alkaline metal alcoholates such as potassium tert.-butylate. Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, alcohols such as tert.-butanol; or a mixture comprising two or more of them.

In a variant of the two-step process (III→II→I), the compounds of formula I may be obtained by a single-vessel reaction from compounds of formula III, without isolation and purification of the intermediate compounds of formula II.

The acetic acid esters of formula III may be obtained from compounds of formula IV (IV)

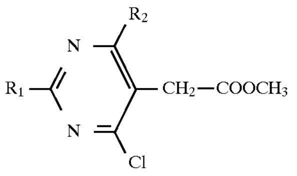

wherein $R_1$ and $R_2$ are as defined above, by reacting it with a hydroxy-pyrazole of formulae V or VI (V)

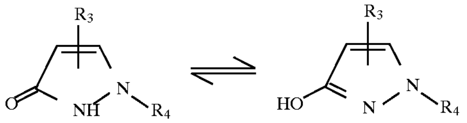

(VI)

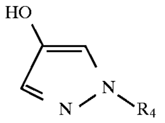

wherein $R_3$and $R_4$ are as defined above in the presence of a base and an inert solvent. Suitable bases and solvents are as for (II→I).

The compounds of formula IV wherein $R_2$ is hydrogen, alkyl, alkoxy, or dialkylamino are known from EP-A-634 495 and EP-A-667 343.

The compounds of formula IV wherein $R_2$ is alkylthio may be obtained by reacting a compound of formula VII

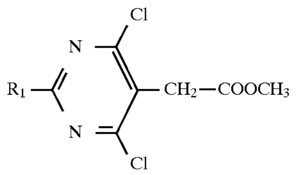

(VII)

wherein $R_1$ is as defined above with a mercaptane of formula VIII $$H—S—R_2 \qquad (VIII)$$

wherein $R_2$ is as defined above, in the presence of a base.

This reaction is preferably carried out in an inert solvent such as an ether, e.g. glyme (dimethoxyethane). Suitable bases are sodium hydride, sodium methylate or the like. In a preferred variant the base is reacted with the mercaptane first to give the sodium salt, which may then be reacted with the compound of formula VII without the presence of a base.

Alternatively the intermediates of formula III wherein $R_2$ is $C_{1-4}$alkoxy or di-$C_{1-4}$alkylamino may be obtained by reacting the starting material dichloropyrimidinyl acetic esters of formula VII with a hydroxypyrazole of formulae V or VI first, and reacting the obtained intermediates of formula IX

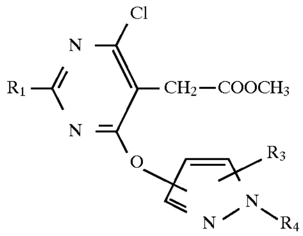

(IX)

wherein $R_1$, $R_3$ and $R_4$ are as defined above, with a compound of formula X $$H—R_2 \qquad (X)$$

wherein $R_2$ is $C_{1-4}$alkyloxy or di-$C_{1-4}$alkylamino, in the presence of a base.

The reaction conditions for this synthesis variant (VII+V/VI→IX+X→III) are similar to those given for the reaction of VII with VIII.

The intermediates of formulae II, III and IX have especially been developed for the synthesis of compounds of formula I. They therefore constitute a part of present invention.

The starting materials of formulae, IV, V, VI, VII and VIII are known, or may be prepared in analogy to known processes.

The compounds of formula V wherein $R_4$ is aryl or heteroaryl, each optionally substituted, may preferably be obtained by using a new oxidation procedure which has been especially developed for the synthesis of the compounds of formula I. It is therefore part of the present invention.

The new oxidation procedure for preparing the compounds of formula V, wherein $R_4$ is aryl or heteroaryl, each optionally substituted comprises oxidising the parent aryl- or heteroarylpyrazolidone of formula XI

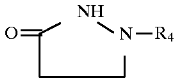

(XI)

wherein $R_4$ is aryl or heteroaryl, each optionally substituted, with an oxidising agent, prepared in situ from $H_2O_2$ and a catalyst.

The oxidation step (XI→V) is preferably carried out in an inert solvent, like formic acid or acetic acid, at low temperatures. Preferably, the exothermic oxidation process is controlled by cooling, or by controlled addition of the oxidising agent. Temperatures are preferably kept below +50° C., especially in the range of 0° C. to +30° C. Suitable oxidising agents are $H_2O_2$ in the presence of oxidation catalysts. Suitable oxidation catalysts are vanadyl acetylacetonate, copper (II) acetylacetonate, manganese oxide ($MnO_2$), selenium oxide ($SeO_2$), nickel oxide ($NiO_2$), and the like.

The compounds of formula I are effective against phytopathogens, including phytopathogenic fungi.

Their advantageous fungicidal activity is established by in vivo tests with test concentrations from 0.1 to 500 mg a.i./l against *Uromyces appendiculatus* on pole beans, against *Puccinia triticina* on wheat, against *Sphaerotheca fuliginea* on cucumber, against *Erysiphe graminis* on wheat and barley, against *Podosphaera leucotricha* on apple, against *Uncinula necator* on grape vine, against *Leptosphaeria nodorum* on wheat, against *Cochliobolus sativus* and *Pyrenophora graminea* on barley, against *Venturia inaequalis* on apple, against *Phytophthora infestans* on tomato and against *Plasmopara viticola* on grape vine.

Many of the compounds of formula I have an excellent plant tolerance and a systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; and Ascomycetes of the order Erysiphales (powdery mildew) such as Erysiphe ssp, Podosphaera spp, Uncinula spp, Sphaerotheca spp; as well as Cochliobolus; Pyrenophora spp; Venturia spp; Mycosphaerella spp; Leptosphaeria; Deuteromycetes such as Pyricularia, Pellicularia (Corticium), Botrytis; and Oomycetes such as Phytophthora spp, Plasmopara spp.

The compounds of formula I are particularly effective against powdery mildew and rust, pyrenophora and leptosphaeria fungi, in particular against pathogens of monocotyledoneous plants such as cereals, including wheat and barley.

The amount of compound of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

In general, satisfactory results are obtained, if the compounds of the invention are applied in an amount of from about 0.01 to 2.0, preferably about 0.02 to 1 kg/ha, in the case of a plant or soil treatment; e.g. 0.04 to 0.500 kg of active ingredient (a.i.) per ha in field crops such as cereals, or concentrations of 4 to 50 g of a.i. per hl in crops such as fruits, vineyards and vegetables (at an application volume of from 300 to 1000 l/ha—depending on the size or leaf volume of the crop—which is equivalent to an application rate of approximately 30–500 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and in cereals (e.g. wheat, oats, barley, rice).

The invention also provides fungicidal compositions, comprising as a fungicide a compound of formula I in association with a agriculturally acceptable diluent (hereinafter diluent). They are obtained in conventional manner, e.g. by mixing a compound of the invention with a diluent and optionally additional ingredients, such as surfactants. The term diluents as used herein means liquid or solid agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and from 10 to 99.99% diluent(s). Concentrated forms of composition, e.g. emulsion concentrates, contain in general from about 2 to 90%, preferably from between 5 and 70% by weight of active agent. Application forms of formulation contain in general from 0.0005 to 10% by weight of a compound of the invention as active agent typical spray-suspensions may, for example, contain from 0.0005 to 0.05, e.g. 0.0001, 0.002 or 0.005% by weight of active agent.

In addition to the usual diluents and surfactants, the compositions of the invention may comprise further additives with special purposes, e.g. stabilisers, desactivators (for solid formulations or carriers with an active surface), agents for improving the adhesion to plants, corrosion inhibitors, anti-foaming agents and colorants. Moreover, further fungicides with similar or complementary fungicidal activity, e.g. sulphur, chlorothalonil, euparen; a guanidine fungicide such as guazatine; dithiocarbamates such as mancozeb, maneb, zineb, propineb; trichloromethane sulphenylphthalimides and analogues such as captan, captafol and folpet; benzimidazoles such as carbendazim, benomyl; azoles such as cyproconazole, flusilazole, flutriafol, hexaconazole, propiconazole, tebuconazole, epoxiconazole, triticonazole, prochloraz; morpholines such as fenpropimorph, fenpropidine, or other beneficially-acting materials, such as cymoxanil, oxadixyl, metalaxyl, or insecticides may be present in the formulations.

Examples of plant fungicide formulations are as follows:

a. Wettable Powder Formulation

10 Parts of a compound of formula I are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 parts by weight of a compound of formula I invention are then added and thorough mixing continued to obtain a granulate formulation with a particle size in the range of from 0.3 to 0.7 mm (where required, the granules may be dried by the addition of 1 to 5% by weight of talcum). The granules may be applied by incorporation into the soil adjacent to the plants to be treated.

c. Emulsion Concentrate

10 Parts by weight of a compound of formula I are mixed with 10 parts of weight of an emulsifier and 80 parts by weight of xylene. The thus obtained concentrate is diluted with water to form an emulsion of the desired concentration, prior to application.

d. Seed Dressing

45 Parts of a compound of formula I are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherence and may be applied to seeds, e.g. by mixing for 2 to 5 minutes in a slowly turning vessel.

The following examples further illustrate the present invention. All temperatures are in centigrade.

EXAMPLE 1

Methyl 2-[2,4-dimethyl-6-(1-phenyl-1H-pyrazol-3-yloxy)-pyrimidin-5-yl]-3-methoxyacrylate

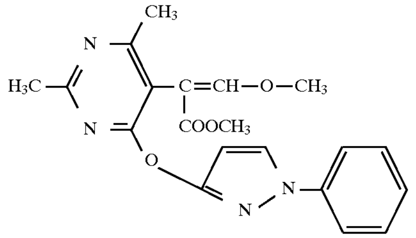

a) Methyl 2-[2,4-dimethyl-6-(1-phenyl-1H-pyrazol-3-yloxy)-pyrimidin-5-yl]-acetate

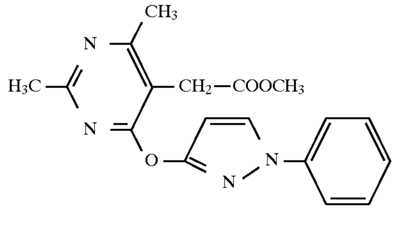

A mixture of methyl (4-chloro-2,6-dimethyl-5-pyrimidinyl)-acetate (5.0 g, 23 mmol), 1-phenyl-1H-pyrazol-3-on (3.73 g, 23 mmol), potassium carbonate (5,5 g, 40 mmol) in dimethylformamide (30 ml) is heated at +120° C. for 2 hours. Addition of water, extraction with ether and drying gives the intermediate methyl 2-[2,4-dimethyl-6-(1-phenyl-1H-pyrazol-3-yloxy)-pyrimidin-5-yl]-acetate as a yellow oil.

$^1$H-NMR ($CDCl_3$): 7.86 (d,1H); 7,67–7.20(m,5H); 6.32 (d,2H); 3.80 (s,2H); 3.70 (s,3H); 2.57(s,3H); 2.36 (s,3H).

b) The intermediate methyl 2-[2,4-dimethyl-6-(1-phenyl-1H-pyrazol-3-yloxy)-pyrimidin-5-yl]-acetate (6.8 g, 20 mmol), NaH (0.8 g of a 80% suspension in oil, 25 mmol) and N,N-diformylmethylamine (5 ml) in dimethylformamide (40 ml) is stirred at 45° C. for two hours. Dimethylsulfate (2.4 ml, 25 mmol) is added at room temperature and stirring is continued for additional two hours. Dilution with ether, washing with brine, drying and chromatography on silicagel (eluant: ethyl, acetate/hexane 1:1) gives methyl 2-[2,4-dimethyl-6-(1-phenyl-1H-pyrazol-3-yloxy)-pyrimidin-5-yl]-3-methoxyacrylate as a colorless oil.

$^1$H-NMR ($CDCl_3$): 7.86 (d,1H); 7.63 (s,1H); 7.67–7.20 (m,5H); 6.32 (d,1H); 3.88 (s,3H); 3.70 (s,3H); 2.57 (s,3H); 2.36 (s,3H).

EXAMPLE 2

Methyl 2-methoximino-[2-methyl-4-dimethylamino-6-(1-phenyl-1H-pyrazol-3-yloxy)-pyrimidin-5-yl]-acetate

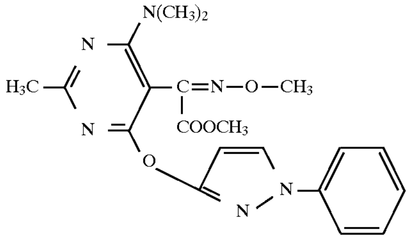

a) Methyl 2-[2-methyl-4-dimethylamino-6-(1-phenyl-1H-pyrazol-3-yloxy)-pyrimidin-5-yl]-acetate

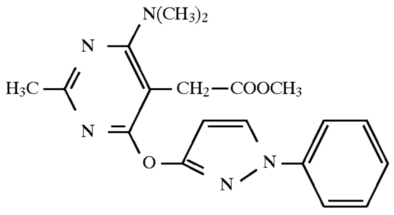

A mixture of methyl (4,6-dichloro-2-methyl-pyrimidin-5-yl )-acetate (5.43 g, 23 mmol), 1-phenyl-1H-pyrazol-3-on (3.73 g, 23 mmol) and potassium carbonate (5.5 g, 40 mmol) in dimethylformamide (30 ml) is heated at +120° C. for 30 minutes. Addition of dimethylamine (10 ml of a 25% aqueous solution) at room temperature, stirring for 20 hours and workup gives the intermediate methyl 2-[2-methyl-4-dimethylamino-6-(1-phenyl-1H-pyrazol-3-yloxy)-pyrimidin-5-yl]-acetate as an oil.

b) Methyl 2-hydroximino-2-[2-methyl-4-dimethylamino-6-(1-phenyl-1H-pyrazol-3-yloxy)-pyrimidin-5-yl]-acetate

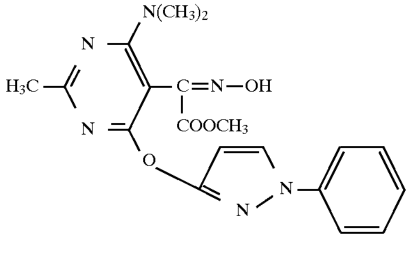

A solution of methyl 2-[2-methyl-4-dimethylamino-6-(1-phenyl-1H-pyrazol-3-yloxy)-pyrimidin-5-yl]-acetate (8.0 g, 22 mmol) in dimethoxyethane (20 ml) is added to a solution of t-BuOK (7.3 g, 65 mmol) and t-BuONO (8 ml) in dimethoxyethane (80 ml) at 40° C. After stirring for 30 minutes the mixture is quenched with ammonium chloride (aqueous solution, 75 ml). The mixture is stirred for two hours. Extraction with ether, drying and chromatography on silicagel (eluant:ethyl acetate/hexane 1:1) gives the crystalline methyl 2-hydroximino-2-[2-methyl-4-dimethylamino-6-(1-phenyl-1H-pyrazol-3-yloxy)-pyrimidin-5-yl]-acetate.

c) The methyl 2-hydroximino-2-[2-methyl-4-dimethylamino-6-(1-phenyl-1H-pyrazol-3-yloxy)-pyrimidin-5-yl]-acetate (3.5 g, 8.8 mmol) is added to a suspension of NaH (0.3 g, 10 mmol) in dimethylformamide (30 ml) and dimethylsulfate (0.9 ml, 9.7 mmol). The mixture is stirred at room temperature for 2 hours. Dilution with ether washing with brine, drying and chromatography on silicagel (eluant ethyl acetate/hexane 1:1) gives methyl 2-methoximino-2-[2-methyl-4-dimethylamino-6-(1-phenyl-1H-pyrazol-3-yloxy)-pyrimidin-5-yl]-acetate.

$^1$H-NMR ($CDCl_3$): 7.82 (d,1H); 7.67–7.20(m,5H); 6.22 (d,2H); 4.06 (s,3H); 3.88 (s,3H); 3.03 (s,6H); 2.41 (s,3H).

EXAMPLE 3

Methyl 2-[2,4-dimethyl-(1-(2,6-dichlorobenzyl)-1H-pyrazol-3-yloxy)-pyrimidin-5-yl]-3-methoxy-acrylate

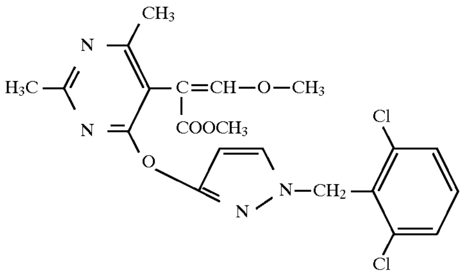

a) Methyl 2-[2,4-dimethyl-6-(1-(2,6-dichlorobenzyl)-1H-pyrazol-3-yloxy)-pyrimidin-5-yl]-acetate

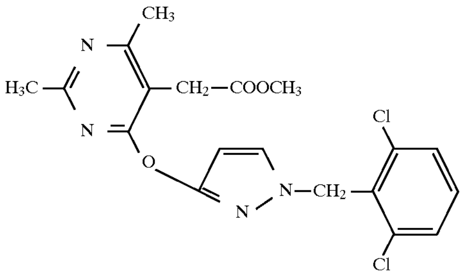

A mixture of methyl (2,4-dimethyl-6-chloro-5-pyrimidinyl)-acetate (0.5 g, 23 mmol), 1-(2,6-dichlorobenzyl)-1H-pyrazol-3-on (5.80 g, 23 mmol) and potassium carbonate (10.0 g, 70 mmol) in dimethylformamide (30 ml) is heated at +130° C. for 2 hours. Addition of water, extraction with ether and drying gives the intermediate methyl 2-[2,4-dimethyl-6-(1-(2,6-dichlorobenzyl)-1H-pyrazol-3-yloxy)-pyrimidin-5-yl]-acetate as a yellow oil.

b) The intermediate methyl 2-[2,4-dimethyl-6-(1-(2,6-dichlorobenzyl)-1H-pyrazol-3-yloxy)-pyrimidin-5-yl]-acetate (9,6 g, 23 mmol) is dissolved in dimethylformamide (20 ml) and added at +30° C. to a suspension of NaH (1.3 g, of a 80% suspension in oil, 46 mmol) and N,N-diformylmethylamine (10 ml) in dimethylformamide (40 ml). The mixture is stirred for 2 hours at +45° C. Dimethylsulfate (2,4 ml, 25 mmol) is added at room temperature with cooling and stirring is continued for additional two hours. Dilution with ether, washing with brine, drying and chromatography on silicagel (eluant:ethyl acetate/hexane 3:1) gives methyl 2-[2,4-dimethyl-6-(1-(2,6-dichlorobenzyl)-1H-pyrazol-3-yloxy)-pyrimidin-5-yl]-3-methoxyacrylate as a colorless oil (4.8 g).

$^1$H-NMR ($CDCl_3$): 7.59(s,1H); 7.39–7.23(m,3H); 7.19(d, 1H); 6.04(d,1H); 5.54(s,2H); 3.83(s,3H); 3.67(s,3H); 2.53 (s,3H); 2.33(s,3H).

EXAMPLE 4

Methyl 2-[2,4-dimethyl-6-(1-(2-methylphenyl)-1H-pyrazol-4-yloxy)-pyrimidin-5-yl]-3-methoxyacrylate

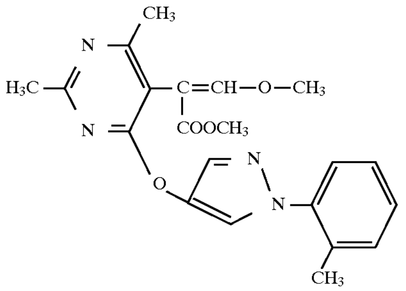

a) Methyl 2-[2,4-dimethyl-6-(1-(2-methylphenyl)-1H-pyrazol-4-yloxy)-pyrimidin-5-yl]-acetate

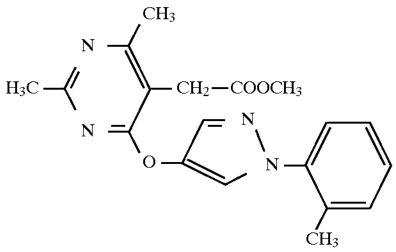

A mixture of methyl (4-chloro-2,6-dimethyl-5-pyrimidinyl)-acetate (4.6 g, 21 mmol), 1-(2-methylphenyl)-1H-pyrazol-4-on (4.1 g, 23 mmol) and potassium carbonate (6.4 g, 46 mmol) in dimethylformamide (50 ml) is heated at +120° C. for 2 hours. Addition of water, extraction with ether and drying gives the intermediate methyl 2-[2,4-dimethyl-6-(1-(2-methylphenyl)-1H-pyrazol4-yloxy)-pyrimidin-5-yl]-acetate as an oil.

$^1$H-NMR ($CDCl_3$): 7.23–7.96(m, 6H); 3.78(s, 2H); 3.73 (s,3H); 2.58(s,3H); 2.47(s, 3H); 2.29 (s,3H).

b) The intermediate methyl 2-[2,4-dimethyl-6-(1-(2-methylphenyl)-1H-pyrazol-4-yloxy)-pyrimidin-5-yl]-acetate (6.0 g, 17 mmol), sodium hydride (0.9 g, 37 mmol) and N,N-diformylmethylamine (6 ml) in a mixture of dimethylformamide (20 ml) and 1,2-dimethoxyethane (20 ml) is stirred at 45° C. for 3 hours. Methyliodide (4.2 g, 30 mmol) is added at room temperature and stirring is continued for additional 16 hours. Dilution with ether, washing with brine, drying and chromatography on silicagel (eluant ethyl acetate/hexane 3:7) gives methyl 2-[2,4-dimethyl-6-(1-(2-methylphenyl)-1H-pyrazole-4-yloxy)-pyrimidin-5-yl]-3-methoxyacrylate as a colorless oil.

$^1$H-NMR($CDCl_3$): 7.26–7.95(m,6H); 3.90(s,3H); 3.74(s, 3H); 2.59(s,3H); 2.38(s,3H) 2.33(s,3H).

EXAMPLE 5

1-(2,5-Dichlorophenyl)-2-pyrazolone

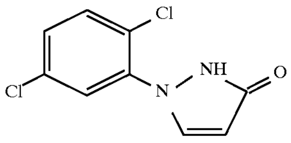

a) 1-(2,5-Dichlorophenyl)-3-pyrazolidone

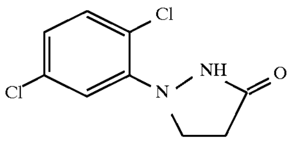

2,5-Dichlorophenylhydrazine hydrochloride (240 g, 1.1 mol) and acrylamide (100 g, 1.4 mol) is refluxed in a solution of sodium (56 g, 2.4 mol) in ethanol (1000 ml) and toluene (1000 ml) for 3 hours. Evaporation of the solvents, acidification with acetic acid dilution with water, filtration and drying (high vacuum, +100° C.) gives the 1-(2,5-dichlorophenyl)-3-pyrazolidone.

b) Hydrogen peroxide (30% solution in water, 120 ml) is slowly added to a well stirred suspension of 1-(2,5-dichlorophenyl)-3-pyrazolidone (200 g, 0.86 mol) and selenium dioxide (3.0 g) in acetic acid (1000 ml). The temperature is controlled by cooling, not to exceed +50° C. After stirring at this temperature for 1 hour crushed ice and water is added. The product is filtered and dried yielding 1-(2,5-dichlorophenyl)-3-pyrazolone, m.p. 201°–202° C.

EXAMPLE 6

1-Phenyl-3-pyrazolidone

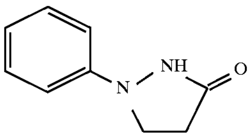

Phenylhydrazine (10.8 g, 0.1 mol), and acrylamide (7.8 g, 0.11 mol), pulverized potassium hydroxide (12.5 g, 0.22) and a catalytic amount of tetrabutylammonium bromide is refluxed for 30 minutes. The precipitate is filtered and washed with toluene. The crystalline sold is dissolved in water. Acidification with acetic acid, filtration and drying gives 1-phenyl-3-pyrazolidone.

The compounds of the following tables are obtained in analogous manner:

TABLE 1

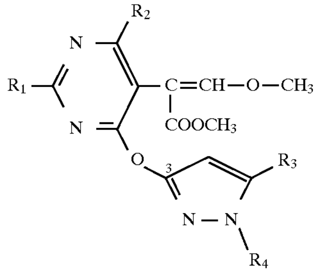

| Comp. No. | $R_1$ | $R_2$ | $R_3$ | $R_4$ | physical data $^1H-NMR$ ($CDCl_3$) or/and m.p. |
|---|---|---|---|---|---|
| 1.01 | $CH_3$ | $CH_3$ | $CH_3$ | 2,3-dichlorophenyl | 7.58(s, 1H); 7.57–7.27(m, 3H); 6.17(s, 1H); 3.85(s, 3H); 3.70(s, 3H); 2.62(s, 3H); 2.32(s, 3H); 2.18(s, 3H). m.p. 169–171° C. |
| 1.02 | $CH_3$ | $CH_3$ | $CH_3$ | 2-chlorophenyl | 7.58(s, 1H); 7.54–7.30(m, 4H); 6.17(s, 1H); 3.85(s, 3H); 3.70(s, 3H); 2.58(s, 3H); 2.35(s, 3H); 2.18(s, 3H). m.p. 135–137° C. |
| 1.03 | $CH_3$ | $CH_3$ | $CH_3$ | 2,4-dichlorophenyl | 7.59(s, 1H); 7.55–7.25(m, 3H); 6.12(s, 1H); 3.85(s, 3H); 3.65(s, 3H); 2.58(s, 3H); 2.33(s, 3H); 2.17(s, 3H). |
| 1.04 | $CH_3$ | $CH_3$ | $CH_3$ | 2,5-dichlorophenyl | 7.59(s, 1H); 7.49–7.35(m, 3H); 7.24(s, 1H); 6.14(s, 1H); 3.85(s, 3H); 3.68(s, 3H); 2.58(s, 3H); 2.32(s, 3H); 2.18(s, 3H). m.p. 142–144° C. |
| 1.05 | $CH_3$ | $CH_3$ | $CH_3$ | 2,6-dichlorophenyl | 7.59(s, 1H); 7,47–7.23(m, 3H); 6.18(s, 1H); 3.83(s, 3H); 3.68(s, 3H); 2.57(s, 3H); 2.33(s, 3H); 2.12(3, 3H). |
| 1.06 | $CH_3$ | $CH_3$ | $CH_3$ | 2,4,5-trichlorophenyl | 7.65(s, 1H); 7.62–7.40(m, 2H); 6.14(s, 1H); 3.86(s, 3H); 3.69(s, 3H); 2.58(s, 3H); 2.34(s, 3H); 2.18(s, 3H). |
| 1.07 | $CH_3$ | $CH_3$ | $CH_3$ | 2,4,6-trichlorophenyl | 7.59(s, 1H); 7.43(s, 2H); 6.18(s, 1H); 3.84(s, 3H); 3.68(s, 3H); 2.55(s, 3H); 2.33(s, 3H); 2.12(s, 3H). |
| 1.08 | $CH_3$ | $CH_3$ | $CH_3$ | 2-$CF_3$-phenyl | 7.52(s, 1H); 7.76–7.34 (m, 3H); 6.06(s, 1H); 3.79(s, 3H); 3.63(s, 3H); 2.52(s, 3H); 2.29(s, 3H); 2.04(s, 3H). m.p. 143–144° C. |
| 1.09 | $CH_3$ | $CH_3$ | $CH_3$ | 2-fluorophenyl | 7.59(s, 1H); 7.52–7.18(m, 3H); 6.13(s, 1H); 3.87(s, 3H); 3.70(s, 3H); 2.59(s, 3H); 2.34(s, 3H); 2.22(s, 3H). |
| 1.10 | $CH_3$ | $CH_3$ | $CH_3$ | 2-methyl-5-chlorophenyl | 7.59(s, 1H); 7.34–7.22(m, 3H); 6.10(s, 1H); 3.86(s, 3H); 3.69(s, 3H); 2.58(s, 3H); 2.33(s, 3H); 2.09(s, 3H). m.p. 139–141° C. |
| 1.11 | $CH_3$ | $CH_3$ | $CH_3$ | phenyl | 7.59(s, 1H); 7.48–7.32(m, 5H); 6.09(s, 1H); 3.85(s, 3H); 3.69(s, 3H); 2.58(s. 3H); 2.33(s, 3H); 2.22(s, 3H). |
| 1.12 | $CH_3$ | $CH_3$ | H | phenyl | 7.86(d, 1H); 7.63(s, 1H); 7.67–7.20(m, 5H); |

TABLE 1-continued

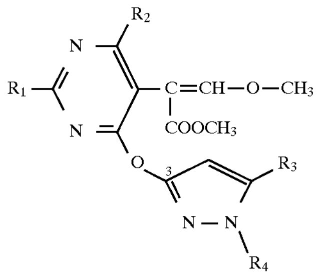

| Comp. No. | $R_1$ | $R_2$ | $R_3$ | $R_4$ | physical data $^1H-NMR$ ($CDCl_3$) or/and m.p. |
|---|---|---|---|---|---|
| | | | | | 6.32(d, 2H); 3.88(s, 3H); 3.70(s, 3H); 2.57(s, 3H); 2.36(s, 3H). |
| 1.13 | $CH_3$ | $CH_3$ | H | 2-chlorophenyl | 7.86(d, 1H); 7.63(s, 1H); 7.67–7.24(m, 5H); 6.37(d, 2H); 3.88(s, 3H); 3.74(s, 3H); 2.58(s, 3H); 2.37(s, 3H). m.p. 150–151° C. |
| 1.14 | $CH_3$ | $CH_3$ | H | 2,4-dichlorophenyl | 7.82(d, 1H); 7.60(s, 1H); 7.58–7.30(m, 3H); 6.37(d, 1H); 3.87(s, 3H); 3.70(s, 3H); 2.58(s, 3H); 2.37(s, 3H). |
| 1.15 | $CH_3$ | $CH_3$ | H | 2-fluorophenyl | 7.97(d, 1H); 7.92–7.17(m, 4H); 7.62(s, 1H); 6.33(d, 1H); 3.90(s, 3H); 3.72(s, 3H); 2.58(s, 3H); 2.37(s.3H). m.p. 150–151° C. |
| 1.16 | $CH_3$ | $CH_3$ | H | benzyl | 7.59(s, 1H); 7.38–7.20(m, 6H); 6.09(d, 1H); 5.22(s, 2H); 3.87(s, 3H); 3.70(s, 3H); 2.57(s, 3H); 2.33(s, 3H). m.p. 130–131° C. |
| 1.17 | $CH_3$ | $CH_3$ | H | 2,6-dichlorobenzyl | 7.59(s, 1H); 7.39–7.23(m, 3H); 7.19(d, 1H); 6.04(d, 1H); 5.54(s, 2H); 3.83(s, 3H); 3.67(s, 3H); 2.53(s, 3H); 2.33(s, 3H). |
| 1.18 | $CH_3$ | $CH_3$ | H | 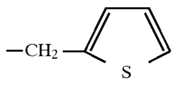 | 7.59(s, 1H); 7.30–6.93(m, 4H); 6.08(d, 1H); 5.34(s, 2H); 3.85(s, 3H); 3.69(s, 3H); 2.53(s, 3H); 2.33(s, 3H). m.p. 115–117° C. |
| 1.19 | $CH_3$ | $CH_3$ | H | 3-methoxybenzyl | 7.59(s, 1H); 7.24(d, 1H); 7.22–6.78(m, 4H); 6.07(d, 1H); 5.17(s, 2H); 3.84(s, 3H); 3.78(s, 3H); 3.70(s, 3H); 2.57(s, 3H); 2.35(s, 3H). |
| 1.20 | $CH_3$ | $CH_3$ | H | 4-methoxybenzyl | 7.60(s, 1H); 7.24(d, 1H); 7.22–6.84(m, 4H); 6.07(d, 1H); 5.15(s, 2H); 3.85(s, 3H); 3.80(s, 3H); 3.70(s, 3H); 2.56(s, 3H); 2.35(s, 3H). |
| 1.21 | $CH_3$ | $N(CH_3)_2$ | H | phenyl | |
| 1.22 | $CH_3$ | $CH_3$ | $CH_3$ | 2-cyanophenyl | 7.80–7.48(m, 4H); 7.59(s, 1H); 6.20(s, 1H); 3.85(s, 3H); 3.70(s, 3H); 2.58(s, 3H); 2.37(s, 3H); 2.30(s, 3H). m.p. 154–156° C. |
| 1.23 | $CH_3$ | $CH_3$ | $CH_3$ | 3-chlorophenyl | 7.60(s, 1H); 7.52–7.32(m, 4H); 6.10(s, 1H); 3.85(s, 3H); 3.69(s, 3H); |

TABLE 1-continued

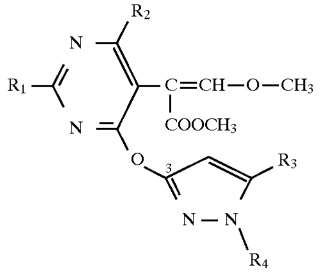

| Comp. No. | $R_1$ | $R_2$ | $R_3$ | $R_4$ | physical data $^1H$—NMR ($CDCl_3$) or/and m.p. |
|---|---|---|---|---|---|
| | | | | | 2.58(s, 3H); 2.39(s, 3H); 2.37(s, 3H). m.p. 135–136° C. |
| 1.24 | $CH_3$ | $CH_3$ | $CH_3$ | 3-$CF_3$-phenyl | 7.79–7.57(m, 4H); 7.59(s, 1H); 6.13(s, 1H); 3.87(s, 3H); 3.70(s, 3H); 2.58(s, 3H); 2.40(s, 3H); 2.37(s, 3H). |
| 1.25 | $CH_3$ | $CH_3$ | $CH_3$ | 2-nitrophenyl | 8.00(dd, 1H); 7.75–7.54(m, 3H); 7.59(s, 1H); 6.16(s, 1H); 3.85(s, 3H); 3.70(s, 3H); 2.59(s, 3H); 2.37(s, 3H); 2.22(s, 3H). m.p. 110–111° C. |
| 1.26 | $CH_3$ | $CH_3$ | $CH_3$ | 2-methoxy-5-chloro-phenyl | 7.59(s, 1H); 7.40–6.91(m, 3H); 6.08(s, 1H); 3.86(s, 3H); 3.80(s, 3H); 370(s, 3H); 2.60(s, 3H); 2.37(s, 3H); 2.18(s, 3H). m.p. 140–141° C. |
| 1.27 | $CH_3$ | $CH_3$ | H | 2-methylphenyl | 7.62(s, 1H); 7.50(d, 1H); 7.38–7.22(m, 4H); 6.33(d, 1H); 3.85(s, 3H); 3.70(s, 3H); 2.57(s, 3H); 2.36(s, 3H); 2.31(s, 3H). m.p. 160–161° C. |
| 1.28 | $CH_3$ | $CH_3$ | $CH_3$ | 3,4-diclorophenyl | 7.63–7.33(m, 3H); 7.62(s, 1H); 6.12(s, 1H); 3.86(s, 3H); 3.70(s, 3H); 2.58(s, 3H); 2.40(s, 3H); 2.37(s, 3H). m.p. 126–129° C. |
| 1.29 | $CH_3$ | $CH_3$ | $CH_3$ | 3-nitrophenyl | 8.38–7.62(m, 4H); 7.60(s, 1H); 6.17(s, 1H); 3.88(s, 3H); 3.73(s, 3H); 2.60(s, 3H); 2.47(s, 3H); 2.37(s, 3H). m.p. 146–147° C. |
| 1.30 | $CH_3$ | $CH_3$ | $CH_3$ | 3-$CF_3$-4-chloro-phenyl | 7.83–7.57(m, 3H); 7.60(s, 1H); 6.14(s, 1H); 3.85(s, 3H); 3.70(s, 3H); 2.58(s, 3H); 2.40(s, 3H); 2.37(s, 3H). m.p. 125–128° C. |
| 1.31 | $CH_3$ | $OCH_3$ | H | 2-chlorophenyl | 7.82(d, 1H); 7.63–7.23(m, 4H); 7.56(s, 1H); 6.30(d, 1H); 3.97(s, 3H); 3.82(s, 3H); 3.67(s, 3H); 2.50(s, 3H) m.p. 123–125° C. |
| 1.32 | $CH_3$ | $OCH_3$ | $CH_3$ | 2-chlorophenyl | 7.55(s, 1H); 7.54–7.30(m, 4H); 6.07(s, 1H); 3.93(s, 3H); 3.80(s, 3H); 3.64(s, 3H); 2.50(s, 3H); 2.15(s, 3H). m.p. 141–142° C. |
| 1.33 | $CH_3$ | $OCH_3$ | H | 2-methoxybenzyl | 7.53(s, 1H); 7.33–6.84(m, 5H); 6.02(d, 1H); 5.20(s, 2H); 3.93(s, 3H); 3.83(s, 3H); 3.80(s, 3H); 3.67(s, 3H); 2.47(s, 3H). |

TABLE 1-continued

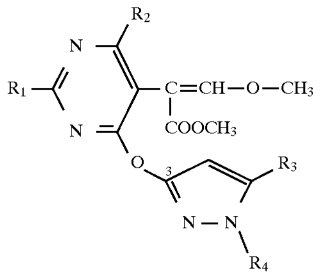

| Comp. No. | $R_1$ | $R_2$ | $R_3$ | $R_4$ | physical data $^1H$—NMR ($CDCl_3$) or/and m.p. |
|---|---|---|---|---|---|
| | | | | | m.p. 110–112° C. |
| 1.34 | $C_2H_5$ | $OCH_3$ | H | 2-methoxybenzyl | 7.55(s, 1H); 7.34–6.84(m, 5H); 6.07(d, 1H); 3.93(s, 3H); 3.82(s, 3H); 3.78(s, 3H); 3.69(s, 3H); 2.75(q, 2H); 1.12(t, 3H). m.p. 80–82° C. |
| 1.35 | $CH_3$ | $OCH_3$ | H | 2-chlorobenzyl | 7.54(s, 1H); 7.39–7.02(m, 5H); 6.07(d, 1H); 5.30(s, 2H); 3.93(s, 3H); 3.80(s, 3H); 3.64(s, 3H); 2.45(s, 3H). m.p. 119–122° C. |
| 1.36 | $C_2H_5$ | $OCH_3$ | H | 2-chlorobenzyl | 7.55(s, 1H); 7.38–7.00(m, 5H); 6.10(d, 1H); 5.30(s, 2H); 3.94(s, 3H); 3.80(s, 3H), 3.70(s, 3H); 2.76(q, 2H); 1.24(t, 3H). m.p. 93–96° C. |
| 1.37 | $CH_3$ | $CH_3$ | H | 2-methoxybenzyl | 7.59(s, 1H); 7.22(d, 1H); 7.20–6.80(m, 4H); 6.08(d, 1H); 5.14(s, 2H); 3.85(s, 3H); 3.80(s, 3H); 3.69(s, 3H); 2.54(s, 3H); 2.33(s, 3H). |
| 1.38 | $CH_3$ | $CH_3$ | H | 2,5-dichlorophenyl | 7.90(d, 1H); 7.68–7.23(m, 3H); 7.61(s, 1H); 6.37(d, 1H); 3.86(s, 3H); 3.70(s, 3H); 2.58(s, 3H); 2.37(s, 3H). m.p. 144–145° C. |
| 1.39 | $CH_3$ | $CH_3$ | H | 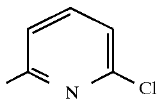 | 8.43(d, 1H); 7.77–7.06(m, 3H); 7.62(s, 1H); 6.30(d, 1H); 3.87(s, 3H); 3.70(s, 3H); 3.55(s, 3H); 2.37(s, 3H). m.p. 127–129° C. |
| 1.40 | $CH_3$ | $CH_3$ | $CH_3$ | 3-methoxyphenyl | 7.58(s, 1H); 7.34–6.85(m, 4H); 6.06(s, 1H); 3.83(s, 3H); 3.80(s, 3H); 3.70(s, 3H); 3.58(s, 3H); 2.38(s, 3H); 2.37(s, 3H). m.p. 101–102° C. |
| 1.41 | $CH_3$ | $CH_3$ | H | 3-chlorophenyl | 7.84(d, 1H); 7.70–7.18(m, 4H); 7.62(s, 1H); 6.31(d, 1H); 3.88(s, 3H); 3.70(s, 3H); 2.57(s, 3H); 2.37(s, 3H). m.p. 120–121° C. |
| 1.42 | $CH_3$ | $CH_3$ | $CH_3$ | 3,5-dichlorophenyl | 7.60(s, 1H); 7.42(d, 2H); 7.33(d, 1H); 6.10(s, 1H); 3.86(s, 3H); 3.70(s, 3H); 2.58(s, 3H); 2.41(s, 3H); 2.36(s, 3H), m.p. 184–185° C. |

TABLE 1-continued

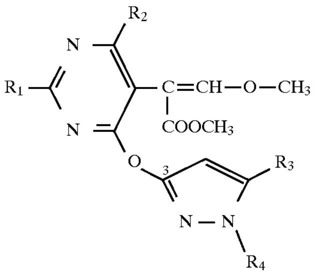

| Comp. No. | $R_1$ | $R_2$ | $R_3$ | $R_4$ | physical data $^1H-NMR$ ($CDCl_3$) or/and m.p. |
|---|---|---|---|---|---|
| 1.43 | $CH_3$ | $SCH_3$ | H | 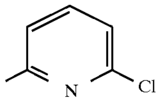 | 8.43(d, 1H); 7.78–7.13(m, 3H); 7.61(s, 1H); 6.27(d, 1H); 3.89(s, 3H); 3.70(s, 3H); 2.57(s, 3H); 2.56(s, 3H). m.p. 148–150° C. |
| 1.44 | $CH_3$ | $OCH_3$ | H | 3-chlorophenyl | 7.83(d, 1H); 7.70–7.17(m, 4H); 7.57(s, 1H); 6.28(d, 1H); 3.94(s, 3H); 3.83(s, 3H); 3.70(s, 3H); 2.50(s, 3H); m.p. 150–151° C. |
| 1.45 | $CH_3$ | $OCH_3$ | H | 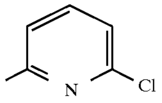 | m.p. 133–135° C. |
| 1.46 | $CH_3$ | $CH_3$ | H | 3-cyanophenyl | |
| 1.47 | $CH_3$ | $CH_3$ | H | 4-biphenylyl | |
| 1.48 | $CH_3$ | $CH_3$ | H | 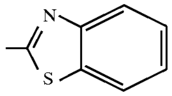 | 8.40(d, 1H); 7.88–7.80(m, 2H); 7.63(s, 1H); 7.52–7.30(m, 2H); 6.41(d, 1H); 3.89(s, 3H); 3.73(s, 3H); 2.58(s, 3H); 2.38(s, 3H). m.p. 178–181° C. |
| 1.49 | $CH_3$ | $CH_3$ | H | 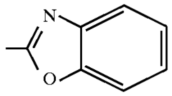 | |
| 1.50 | $CH_3$ | $CH_3$ | H | 3,4-dichlorophenyl | 7.80(d+s, 2H); 7.63(s, 1H); 7.49(s, 2H); 6.35(d, 1H); 3.89(s, 3H); 3.70(s, 3H); 2.58(s, 3,11); 2.38(s, 3H). m.p. 192–194° C. |
| 1.51 | $CH_3$ | $CH_3$ | H | 3-$CF_3$-phenyl | 7.96–7.47(m, 4H); 7.90(d, 1H); 7.63(s, 1H); 6.37(d, 1H); 3.89(s, 3H); 3.70(s, 3H); 3.57(s, 3H); 2.38(s, 3H), m.p. 130° C. |
| 1.52 | $CH_3$ | $CH_3$ | H | 3-methoxyphenyl | |
| 1.53 | $CH_3$ | $CH_3$ | H | 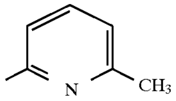 | |
| 1.54 | $CH_3$ | $CH_3$ | H | 2-nitrophenyl | |
| 1.55 | $CH_3$ | $CH_3$ | H | 3-nitrophenyl | |
| 1.56 | $CH_3$ | $CH_3$ | H | 2,6-dichlorophenyl | |
| 1.57 | $CH_3$ | $CH_3$ | $CH_3$ | 5-$CF_3$-2-chloro-phenyl | |
| 1.58 | $CH_3$ | $CH_3$ | $CH_3$ | 4-biphenylyl | |

TABLE 1-continued

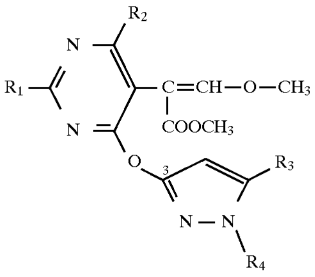

| Comp. No. | $R_1$ | $R_2$ | $R_3$ | $R_4$ | physical data $^1H-NMR$ ($CDCl_3$) or/and m.p. |
|---|---|---|---|---|---|
| 1.59 | $CH_3$ | $CH_3$ | $CH_3$ | 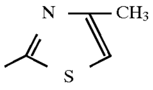 | |
| 1.60 | $CH_3$ | $CH_3$ | $CH_3$ | 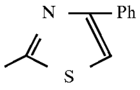 | |
| 1.61 | $CH_3$ | $CH_3$ | $CH_3$ | 3,4-dimethoxyphenyl | |
| 1.62 | $CH_3$ | $CH_3$ | $CH_3$ | 2-pyridyl | |
| 1.63 | $CH_3$ | $CH_3$ | $CH_3$ | 4-phenoxyphenyl | |
| 1.64 | $CH_3$ | $CH_3$ | H | 2-methyl-5-chloro-phenyl | 7.62(s, 1H); 7.53(d, 1H); 7.28–7.19(m, 3H); 6.33(d, 1H); 3.86(s, 3H); 3.70(s, 3H); 2.58(s, 3H); 2.38(s, 3H); 2.34(s, 3H). m.p. 122–123° C. |
| 1.65 | $CH_3$ | $CH_3$ | H | 4-chlorophenyl | 7.82(d, 1H); 7.60(s, 1H); 7.58–7.38(m, 4H); 6.34(d, 1H); 3.88(s, 3H); 3.70(s, 3H); 2.59(s, 3H); 2.39(s, 3H). |
| 1.66 | $CH_3$ | $CH_3$ | $CH_3$ | 3-fluorophenyl | 7.60(s, 1H); 7.42–6.97(m, 4H); 6.08(s, 1H); 3.86(s, 3H); 3.70(s, 3H); 2.58(s, 3H); 2.38(s, 3H); 2.37(s, 3H). m.p. 129–130° C. |
| 1.67 | $CH_3$ | $CH_3$ | $CH_3$ | 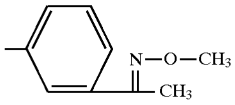 | 7.78(s, 1H); 7.65–7.40(m, 4H); 6.09(s, 1H); 3.97(s, 3H); 3.86(s, 3H); 3.70(s, 3H); 2.60(s, 3H); 2.39(2xs, 6H); 2.26(s, 3H). |
| 1.68 | $CH_3$ | $CH_3$ | $CH_3$ | 4-fluorophenyl | 7.60(s, 1H); 7.43–7.03(m, 4H); 6.08(s, 1H); 3.85(s, 3H); 3.70(s, 3H); 2.60(s, 3H); 2.38(s, 3H); 2.37(s, 3H). |
| 1.69 | $CH_3$ | $CH_3$ | $CH_3$ | 4-chlorophenyl | 7.60(s, 1H); 7.41(s, 4H); 6.06(s, 1H); 3.87(s, 3H); 3.70(s, 3H); 2.59(s, 3H); 2.38(2s, 6H) |
| 1.70 | $CH_3$ | $OCH_3$ | H | 3,4-dichlorophenyl | 7.80(d+s, 2H); 7.58(s, 1H); 7.49(s, 2H); 6.33(d, 1H); 3.97(s, 3H); 3.85(s, 3H); 3.70(s, 3H); 2.50(s, 3H). m.p. 157–159° C. |
| 1.71 | $CH_3$ | $OCH_3$ | $CH_3$ | 3-$CF_3$-phenyl | 7.80–7.53(m, 5H); 6.05(s, 1H); 3.95(s, 3H); 3.83(s, 3H); 3.70(s, 3H); 2.52(s, 3H); 2.38(s, 3H). m.p. 109–111° C. |
| 1.72 | $N(CH_3)_2$ | $CH_3$ | H | 3-chlorophenyl | 7.81(d, 1H); 7.70–7.17(m, 5H); 7.37(d, 1H); 3.85(s, 3H); 3.70(s, 3H); 3.04(s, 6H); 2.23(s, 3H). |

TABLE 1-continued

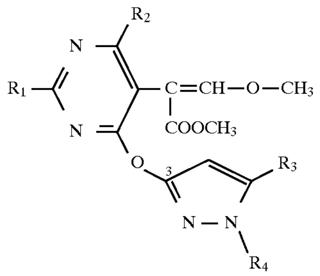

| Comp. No. | $R_1$ | $R_2$ | $R_3$ | $R_4$ | physical data $^1H-NMR$ ($CDCl_3$) or/and m.p. |
|---|---|---|---|---|---|
| 1.73 | $CH_3$ | $OCH_3$ | H | 3-$CF_3$-phenyl | m.p. 163–165° C. 7.96–7.47(m, 6H); 6.33(d, 1H); 3.96(s, 3H); 3.86(s, 3H); 3.70(s, 3H); 2.50(s, 3H). |
| 1.74 | $CH_3$ | $OCH_3$ | H | 2,5-dichlorophenyl | m.p. 152–154° C. 7.90(d, 1H); 7.70–7.23(m, 4H); 6.33(d, 1H); 3.96(s, 3H); 3.84(s, 3H); 3.70(s, 3H); 2.53(s, 3H). |
| 1.75 | H | $CH_3$ | H | 3-$CF_3$-phenyl | 8.64(s, 1H); 7.95(d, 1H); 7.82–7.50(m, 5H); 6.33(d, 1H); 3.93(s, 3H); 3.73(s, 3H); 2.42(s, 3H). |
| 1.76 | $CH_3$ | $OCH_3$ | H | 5-chloro-2-methylphenyl | m.p. 153–155° C. 7.57(s, 1H); 7.50(d, 1H); 7.40–7.18(m, 3H); 6.28(d, 1H); 3.95(s, 1H); 3.83(s, 3H); 3.70(s, 3H); 2.50(s, 3H); 2.32(s, 3H). |
| 1.77 | $CH_3$ | $CH_3$ | $CH_3$ | 3-chloro-2-methylphenyl | m.p. 102–106° C. 7.60(s, 1H); 7.46–7.19(m, 3H); 6.08(s, 1H); 3.83(s, 3H); 3.70(s, 3H); 2.58(s, 3H); 2.37(s, 3H); 2.10(2s, 6H). |
| 1.78 | $CH_3$ | $CH_3$ | $CH_3$ | 4-chloro-2-methylphenyl | m.p. 157–159° C. 7.60(s, 1H); 7.32–7.20(m, 3H); 6.04(s, 1H); 3.84(s, 3H); 3.70(s, 3H); 2.57(s, 3H); 2.36(s, 3H); 2.10(2s, 6H). |
| 1.79 | $CH_3$ | $OCH_3$ | $CH_3$ | 3-chlorophenyl | 7.56(s, 1H); 7.50–7.26(m, 4H); 6.04(s, 1H); 3.93(s, 3H); 3.83(s, 3H); 3.68(s, 3H); 2.53(s, 3H); 2.38(s, 3H). |
| 1.80 | $CH_3$ | $OCH_3$ | $CH_3$ | 4-chlorophenyl | 7.52(s, 1H); 7.38(s, 4H); 6.03(s, 1H); 3.94(s, 3H); 3.82(s, 3H); 3.66(s, 3H); 2.51(s, 3H); 2.36(s, 3H). |
| 1.81 | $CH_3$ | $OCH_3$ | $CH_3$ | 3,4-dichlorophenyl | 7.63–7.30(m, 4H); 6.05(s, 1H); 3.93(s, 3H); 3.82(s, 3H); 3.67(s, 3H), 2.53(s, 3H); 2.38(s, 3H). |
| 1.82 | $CH_3$ | $OCH_3$ | $CH_3$ | 2,3-dichlorophenyl | m.p. 147–148° C. 7.60–7.27(m, 4H); 6.08(s, 1H); 3.92(s, 3H); 3.81(s, 3H); 3.64(s, 3H); 2.50(s, 3H); 2.15(s, 3H). |
| 1.83 | $CH_3$ | $OCH_3$ | $CH_3$ | 3,5-dichlorophenyl | m.p. 147–150° C. 7.52(s, 1H); 7.40–7.28(m, 3H); 6.03(s, 1H); 3.93(s, 3H); 3.80(s, 3H); 3.66(s, 3H); 2.48(s, 3H); 2.38(s, 3H). |
| 1.84 | $CH_3$ | $OCH_3$ | $CH_3$ | 4-chloro-2-methylphenyl | m.p. 160–161° C. 7.52(s, 1H); 7.32–7.20(m, 3H); 6.02(s, 1H); 3.90(s, 3H); 3.83(s, 3H); 3.67(s, 3H); 2.50(s, 3H); |

TABLE 1-continued

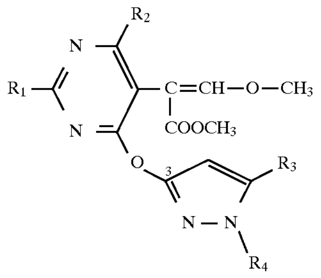

| Comp. No. | $R_1$ | $R_2$ | $R_3$ | $R_4$ | physical data $^1H$—NMR ($CDCl_3$) or/and m.p. |
|---|---|---|---|---|---|
| | | | | | 2.15(2s, 6H). |
| 1.85 | $CH_3$ | $OCH_3$ | $CH_3$ | 3-chloro-2-methylphenyl | m.p. 140–143° C.<br>7.52(s, 1H); 7.45–7.20(m, 3H); 6.03(s, 1H); 3.93(s, 3H); 3.82(s, 3H); 3.68(s, 3H); 2.50(s, 3H); 2.15(s, 3H); 2.14(s, 3H). |
| 1.86 | $CH_3$ | $OCH_3$ | $CH_3$ | 2,4-dichlorophenyl | m.p. 147–149° C.<br>7.52–7.30(m, 4H); 6.08(s, 1H); 3.95(s, 3H); 3.80(s, 3H); 3.68(s, 3H); 2.53(s, 3H); 2.17(s, 3H). |
| 1.87 | $CH_3$ | $OCH_3$ | $CH_3$ | 5-chloro-2-methylphenyl | 7.54(s, 1H); 7.34–7.20(m, 3H); 6.03(s, 1H); 3.92(s, 3H); 3.80(s, 3H); 3.67(s, 3H); 2.52(s, 3H); 2.15(2s, 6H). |
| 1.88 | $CH_3$ | $CH_3$ | $CH_3$ | 3-bromophenyl | 7.65–7.30(m, 5H); 6.10(s, 1H); 3.87(s, 3H); 3.70(s, 3H); 2.59(s, 3H), 2.38(s, 3H); 1.36(s, 3H); |
| 1.89 | $CH_3$ | $CH_3$ | $CH_3$ | 4-bromophenyl | m.p. 141–142° C.<br>7.60(s, 1H); 7.57–7.30(m, 4H); 6.10(s, 1H); 3.85(s, 3H); 3.70(s, 3H); 2.58(s, 3H); 2.38(2s, 6H). |
| 1.90 | $CH_3$ | $OCH_3$ | $CH_3$ | 3-bromophenyl | 7.64–7.26(m, 5H); 6.06(s, 1H); 3.97(s, 3H); 3.83(s, 3H); 3.69(s, 3H); 2.53(s, 3H); 2.38(s, 3H). |
| 1.91 | $CH_3$ | $OCH_3$ | H | 3-bromophenyl | 7.86–7.24(m, 5H); 6.30(d, 1H); 3.97(s, 3H); 3.86(s, 3H); 3.70(s, 3H); 2.53(s, 3H). |
| 1.92 | $CH_3$ | $OCH_3$ | H | 4-methylphenyl | m.p. 144–145° C.<br>7.78(d, 1H); 7.57–7.17(m, 5H); 6.23(d, 1H); 3.97(s, 3H); 3.88(s, 3H); 3.70(s, 3H); 2.52(s, 3H); 2.38(s, 3H). |
| 1.93 | $CH_3$ | $CH_3$ | H | 4-bromophenyl | 7.80(d, 1H); 7.57(s, 1H); 7.55(s, 4H); 6.28(d, 1H); 3.97(s, 3H); 3.86(s, 3H); 3.70(s, 3H); 2.53(s, 3H). |
| 1.94 | $CH_3$ | $OCH_3$ | H | 2,5-dimethylphenyl | 7.56(s, 1H); 7.48(d, 1H); 7.08–7.02(m, 3H); 6.23(d, 1H); 3.96(s, 3H); 3.84(s, 3H); 3.70(s, 3H); 2.52(s, 3H); 2.38(s, 3H); 2.25(s, 3H). |
| 1.95 | $CH_3$ | $CH_3$ | H | 3-bromophenyl | m.p. 86–87° C.<br>7.84(d, 1H); 7.62(s, 1H); 7.57–7.26(m, 4H); 6.33(d, 1H); 3.87(s, 3H); 3.70(s, 3H); 2.58(s, 3H); 2.38(s, 3H). |
| 1.96 | $CH_3$ | $CH_3$ | H | 4-bromophenyl | m.p. 120–122° C.<br>7.83(d, 1H); 7.63(s, 1H); 7.53(s, 4H); 6.33(d, 1H); 3.87(s, 3H); 3.70(s, 3H); 2.58(s, 3H); 2.38(s, 3H). |

TABLE 1-continued

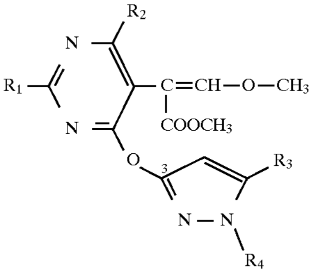

| Comp. No. | $R_1$ | $R_2$ | $R_3$ | $R_4$ | physical data $^1H$—NMR ($CDCl_3$) or/and m.p. |
|---|---|---|---|---|---|
| 1.97 | $CH_3$ | $CH_3$ | H | 4-methylphenyl | m.p. 141–142° C. 7.81(d, 1H); 7.62(s, 1H); 7.50–7.19(m, 4H); 6.29(d, 1H); 3.87(s, 3H); 3.70(s, 3H); 2.58(s, 3H); 2.38(2s, 6H), |
| 1.98 | $CH_3$ | $CH_3$ | H | 2,5-dimethylphenyl | m.p. 121–122° C. 7.60(s, 1H); 7.52(d, 1H); 7.17–7.03(m, 3H); 6.28(d, 1H); 3.84(s, 3H); 3.70(s, 3H); 2.58(s, 3H); 2.38(s, 3H); 2.37(s, 3H); 2.30(s, 3H). |
| 1.99 | $CH_3$ | $CH_3$ | $CH_3$ | 3,5-dimethylphenyl | 7.60(s, 1H); 7.06(s, 2H); 6.96(s, 1H); 6.06(s, 1H); 3.84(s, 3H); 3.70(s, 3H); 2.59(s, 3H); 2.37(4s; 12H). m.p. 143–144° C. |

TABLE 2

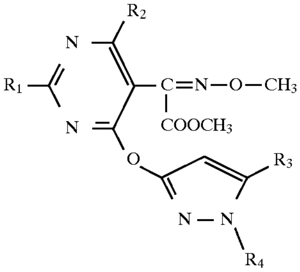

| Comp. No. | $R_1$ | $R_2$ | $R_3$ | $R_4$ | physical data $^1H$—NMR ($CDCl_3$) or/and m.p. |
|---|---|---|---|---|---|
| 2.01 | $CH_3$ | $CH_3$ | $CH_3$ | 2,3-dichlorophenyl | |
| 2.02 | $CH_3$ | $CH_3$ | $CH_3$ | 2-chlorophenyl | |
| 2.03 | $CH_3$ | $CH_3$ | $CH_3$ | 2,4-dichlorophenyl | |
| 2.04 | $CH_3$ | $CH_3$ | $CH_3$ | 2,5-dichlorophenyl | |
| 2.05 | $CH_3$ | $CH_3$ | $CH_3$ | 2,6-dichlorophenyl | |
| 2.06 | $CH_3$ | $CH_3$ | $CH_3$ | 2,4,5-trichlorophenyl | |
| 2.07 | $CH_3$ | $CH_3$ | $CH_3$ | 2,4,6-trichlorophenyl | |
| 2.08 | $CH_3$ | $CH_3$ | $CH_3$ | 2-$CF_3$-phenyl | |
| 2.09 | $CH_3$ | $CH_3$ | $CH_3$ | 2-fluorophenyl | |
| 2.10 | $CH_3$ | $CH_3$ | $CH_3$ | 2-methyl-5-chlorophenyl | |
| 2.11 | $CH_3$ | $CH_3$ | $CH_3$ | phenyl | 7.48–7.32(m, 5H); 6.14(s, 1H); 3.80(s, 2H); 3.69(s, 2H); 2.55(s, 3H); 2.45(s, 3H); 2.37(s, 3H). |
| 2.12 | $CH_3$ | $CH_3$ | H | phenyl | |
| 2.13 | $CH_3$ | $CH_3$ | H | 2-chlorophenyl | |
| 2.14 | $CH_3$ | $CH_3$ | H | 2,4-dichlorophenyl | |
| 2.15 | $CH_3$ | $CH_3$ | H | 2-fluorophenyl | 7.97(d, 1H); 7.90–7.14(m, 4H); 6.30(d, 1H); |

TABLE 2-continued

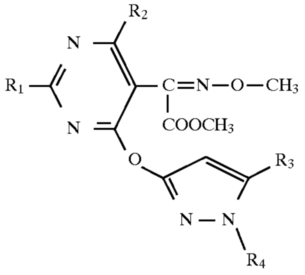

| Comp. No. | $R_1$ | $R_2$ | $R_3$ | $R_4$ | physical data $^1H-NMR$ ($CDCl_3$) or/and m.p. |
|---|---|---|---|---|---|
| | | | | | 3.86(s, 2H); 3.70(s, 3H); 2.57(s, 3H); 2.37(s, 3H). |
| 2.16 | $CH_3$ | $CH_3$ | H | benzyl | |
| 2.17 | $CH_3$ | $CH_3$ | H | 2,6-dichlorobenzyl | |
| 2.18 | $CH_3$ | $CH_3$ | H | 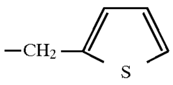 | |
| 2.19 | $CH_3$ | $CH_3$ | H | 3-methoxybenzyl | |
| 2.20 | $CH_3$ | $CH_3$ | H | 4-methoxybenzyl | |
| 2.21 | $CH_3$ | $N(CH_3)_2$ | H | phenyl | 7.82(d, 1H); 7.67–7.20(m, 5H); 6.22(d, 2H); 4.06(s, 3H); 3.88(s, 3H); 3.03(s, 6H); 2.41(s, 3H). |
| 2.22 | $CH_3$ | $CH_3$ | $CH_3$ | 2-cyanophenyl | |
| 2.23 | $CH_3$ | $CH_3$ | $CH_3$ | 3-chlorophenyl | |
| 2.24 | $CH_3$ | $CH_3$ | $CH_3$ | 3-$CF_3$-phenyl | |
| 2.25 | $CH_3$ | $CH_3$ | $CH_3$ | 2-nitrophenyl | |
| 2.26 | $CH_3$ | $CH_3$ | $CH_3$ | 2-methoxy-5-chloro-phenyl | |
| 2.27 | $CH_3$ | $CH_3$ | H | 2-methylphenyl | |
| 2.28 | $CH_3$ | $CH_3$ | $CH_3$ | 3,4-dichlorophenyl | |
| 2.29 | $CH_3$ | $CH_3$ | $CH_3$ | 3-nitrophenyl | |
| 2.30 | $CH_3$ | $CH_3$ | $CH_3$ | 3-$CF_3$-4-chloro-phenyl | |
| 2.31 | $CH_3$ | $OCH_3$ | H | 2-chlorophenyl | |
| 2.32 | $CH_3$ | $OCH_3$ | $CH_3$ | 2-chlorophenyl | |
| 2.33 | $CH_3$ | $OCH_3$ | H | 2-methoxybenzyl | |
| 2.34 | $C_2H_5$ | $OCH_3$ | H | 2-methoxybenzyl | |
| 2.35 | $CH_3$ | $OCH_3$ | H | 2-chlorobenzyl | |
| 2.36 | $C_2H_5$ | $OCH_3$ | H | 2-chlorobenzyl | 7.40–7.03(m, 5H); 6.12(d, 1H); 5.30(s, 2H); 3.95(s, 3H); 3.85(s, 2H); 3.70(s, 3H); 2.75(q, 2H); 1.24(t, 3H). |
| 2.37 | $CH_3$ | $CH_3$ | H | 2-methoxybenzyl | |
| 2.38 | $CH_3$ | $CH_3$ | H | 2,5-dichlorophenyl | |
| 2.39 | $CH_3$ | $CH_3$ | H | 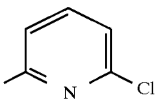 | |
| 2.40 | $CH_3$ | $CH_3$ | $CH_3$ | 3-methoxyphenyl | |
| 2.41 | $CH_3$ | $CH_3$ | H | 3-chlorophenyl | |
| 2.42 | $CH_3$ | $CH_3$ | $CH_3$ | 3,5-dichlorophenyl | |
| 2.43 | $CH_3$ | $SCH_3$ | H | 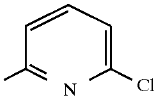 | |
| 2.44 | $CH_3$ | $OCH_3$ | H | 3-chlorophenyl | |
| 2.45 | $CH_3$ | $OCH_3$ | H | 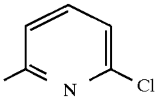 | |

TABLE 2-continued

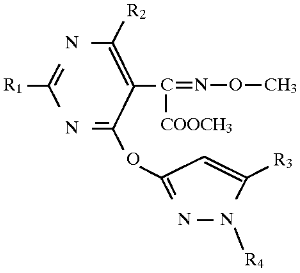

| Comp. No. | $R_1$ | $R_2$ | $R_3$ | $R_4$ | physical data $^1H-NMR$ ($CDCl_3$) or/and m.p. |
|---|---|---|---|---|---|
| 2.46 | $CH_3$ | $CH_3$ | H | 3-cyanophenyl | |
| 2.47 | $CH_3$ | $CH_3$ | H | 4-biphenylyl | |
| 2.48 | $CH_3$ | $CH_3$ | H | 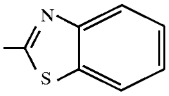 | |
| 2.49 | $CH_3$ | $CH_3$ | H | 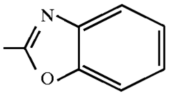 | |
| 2.50 | $CH_3$ | $CH_3$ | H | 3,4-dichlorophenyl | |
| 2.51 | $CH_3$ | $CH_3$ | H | 3-$CF_3$-phenyl | |
| 2.52 | $CH_3$ | $CH_3$ | H | 3-methoxyphenyl | |
| 2.53 | $CH_3$ | $CH_3$ | H | 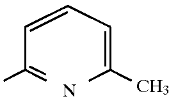 | |
| 2.54 | $CH_3$ | $CH_3$ | H | 2-nitrophenyl | |
| 2.55 | $CH_3$ | $CH_3$ | H | 3-nitrophenyl | |
| 2.56 | $CH_3$ | $CH_3$ | H | 2,6-dichlorophenyl | |
| 2.57 | $CH_3$ | $CH_3$ | $CH_3$ | 5-$CF_3$-2-chloro-phenyl | |
| 2.58 | $CH_3$ | $CH_3$ | $CH_3$ | 4-biphenylyl | |
| 2.59 | $CH_3$ | $CH_3$ | $CH_3$ | 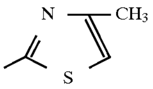 | |
| 2.60 | $CH_3$ | $CH_3$ | $CH_3$ | 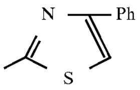 | |
| 2.61 | $CH_3$ | $CH_3$ | $CH_3$ | 3,4-dimethoxyphenyl | |

TABLE 3

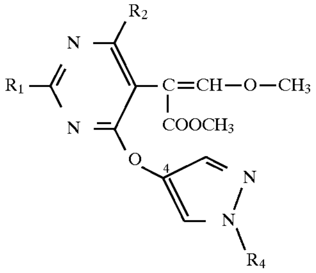

| Comp. No. | $R_1$ | $R_2$ | $R_4$ | physical data $^1H-NMR$ ($CDCl_3$) or/and m.p. |
|---|---|---|---|---|
| 3.01 | $CH_3$ | $CH_3$ | 2,3-dichlorophenyl | 7.22–8.19(m, 5H); 3.92(s, 3H); 3.76(s, 3H); 2.62(s, 3H); 2.37(s, 3H). |
| 3.02 | $CH_3$ | $CH_3$ | 2-chlorophenyl | 7.26–8.21(m, 6H); 3.93(s, 3H); 3.76(s, 3H); 2.62(s, 3H); 2.38(s, 3H). |
| 3.03 | $CH_3$ | $CH_3$ | 2,4-dichlorophenyl | 7.28–8.20(m, 5H); 3.91(s, 3H); 3.77(s, 3H); 2.61(s, 3H); 2.38(s, 3H). |
| 3.04 | $CH_3$ | $CH_3$ | 2,5-dichlorophenyl | 7.24–8.23(m, 5H); 3.93(s, 3H); 3.78(s, 3H); 2.59(s, 3H); 2.37(s, 3H). |
| 3.05 | $CH_3$ | $CH_3$ | 2,6-dichlorophenyl | 7.26–7.97(m, 5H); 3.88(s, 3H); 3.75(s, 3H); 2.60(s, 3H); 2.37(s, 3H). |
| 3.06 | $CH_3$ | $CH_3$ | 2-methylphenyl | 7.26–7.95(m, 6H); 3.90(s, 3H); 3.74(s, 3H); 2.59(s, 3H); 2.38(s, 3H); 2.33(s, 3H). |
| 3.07 | $CH_3$ | $CH_3$ | 2-isopropylphenyl | 7.24–7–96(m, 6H); 3.94(s, 3H); 3.77(s, 3H); 3.03(m, 1H); 2.59(s, 3H); 2.38(s, 3H); 1.23(s, 3H); 1.20(s, 3H). |
| 3.08 | $CH_3$ | $CH_3$ | 2-$CF_3$-phenyl | 7.56–8.18(m, 6H); 3.92(s, 3H); 3.73(s, 3H); 2.63(s, 3H); 2.37(s, 3H); |
| 3.09 | $CH_3$ | $CH_3$ | 2-methoxyphenyl | 7.03–8.28(m, 6H); 3.90(s, 3H); 3.77(s, 3H); 2.60(s, 3H); 2.38(s, 3H); 2.04(s, 3H). |
| 3.10 | $CH_3$ | $CH_3$ | 2-methyl-5-chlorophenyl | 7.22–7–93(m, 5H); 3.90(s, 3H); 3.74(s, 3H); 2.61(s, 3H); 2.38(s, 3H); 2.31(s, 3H). |
| 3.11 | $CH_3$ | $CH_3$ | phenyl | 7.24–8.21(m, 7H); 3.92(s, 3H); 3.75(s, 3H); 2.61(s, 3H); 2.38(s, 3H). |
| 3.12 | $CH_3$ | $CH_3$ | 3-methylphenyl | 6.84–7.59(m, 6H); 3.90(s, 3H); 3.74(s, 3H); 2.51(s, 3H); 2.38(s, 3H). |
| 3.13 | $CH_3$ | $CH_3$ | 2-chloro-4-methylphenyl | 7.16–8.13(m, 5H); 3.94(s, 3H); 3.78(s, 3H); 2.59(s, 3H); 2.50(s, 3H); 2.39(s, 3H). |
| 3.14 | $CH_3$ | $CH_3$ | 2-cyano-4-chlorophenyl | 7.63–8.59(m, 5H); 3.81(s, 3H); 3.76(s, 3H); 2.62(s, 3H); 2.53(2, 3H). |
| 3.15 | $CH_3$ | $CH_3$ | 3-$CF_3$-phenyl | 7.49–8.21(m, 6H); 3.92(s, 3H); 3.74(s, 3H); 2.63(s, 3H); 2.38(s, 3H). |
| 3.16 | $CH_3$ | $CH_3$ | 4-chlorophenyl | 7.39–8.12(m, 6H); 3.89(s, 3H); 3.72(s, 3H); 2.61(s, 3H); 2.37(s, 3H); |
| 3.17 | $CH_3$ | $CH_3$ | 2-cyanophenyl | 7.40–8.58(m, 6H); 3.92(s, 3H); 3.75(s, 3H); 2.62(s, 3H); 2.37(s, 3H). |
| 3.18 | $CH_3$ | $CH_3$ | 2-methyl-3-chlorophenyl | 7.20–7.89(m, 5H); 3.92(s, 3H); 3.74(s, 3H); 2.59(s, 3H); 2.37(s, 3H); |

TABLE 3-continued

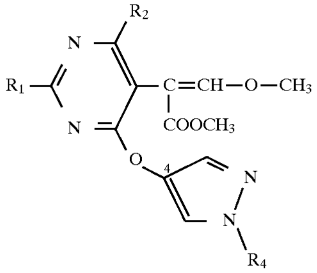

| Comp. No. | $R_1$ | $R_2$ | $R_4$ | physical data $^1H-NMR$ ($CDCl_3$) or/and m.p. |
|---|---|---|---|---|
| | | | | 2.28(s, 3H). |
| 3.19 | $CH_3$ | $CH_3$ | 2-methyl-4-chlorophenyl | 7.22–7.87(m, 5H); 3.93(s, 3H); 3.76(s, 3H); 2.60(s, 3H); 2.39(s, 3H); 2.34(s, 3H). |
| 3.20 | $CH_3$ | $CH_3$ | 2.3-dimethylphenyl | 7.17–7.86(m, 5H); 3.91(s, 3H); 3.76(s, 3H); 2.60(s, 3H); 2.38(s, 6H); 2.15(s, 3H). |
| 3.21 | $CH_3$ | $CH_3$ | 2,6-dimethylphenyl | 7.06–7.64(m, 5H); 3.91(s, 3H); 3.73(s, 3H); 2.44(s, 3H); 2.37(s, 3H); 2.08(s, 6H). |
| 3.22 | $CH_3$ | $CH_3$ | 2-methyl-6-chlorophenyl | 7.28–7.91(m, 5H); 3.94(s, 3H); 3.76(s, 3H); 2.61(s, 3H); 2.39(s, 3H); 2.17(s, 3H). |
| 3.23 | $CH_3$ | $CH_3$ | 4-methylphenyl | 7.23–8.11(m, 6H); 3.91(s, 3H); 3.75(s, 3H); 2.61(s, 3H); 2.39(s, 3H); 2.36(s, 3H). |
| 3.24 | $CH_3$ | $CH_3$ | 2-ethylphenyl | 6.98–7.63(m, 6H); 3.89(s, 3H); 3.74(s, 3H); 2.71(s, 3H); 2.48(s, 3H); 2.37(s, 3H); 1.12(t, 3H). |
| 3.25 | $CH_3$ | $CH_3$ | 2-fluorophenyl | 7.20–8.27(m, 6H); 3.93(s, 3H); 3.74(s, 3H); 2.61(s, 3H); 2.38(s, 3H). |
| 3.26 | $CH_3$ | $CH_3$ | 2-biphenylyl | 7.17–7.64(m, 11H); 3.83(s, 3H); 3.62(s, 3H); 2.47(s, 3H); 2.30(s, 3H). |
| 3.27 | $CH_3$ | $CH_3$ | 3,4-dichlorophenyl | 7.55–8.32(m, 5H); 3.91(s, 3H); 3.73(s, 3H); 2.62(s, 3H); 2.37(s, 3H). |
| 3.28 | $CH_3$ | $CH_3$ | 3,5-dichlorophenyl | 7.23–8.18(m, 5H); 3.91(s, 3H); 3.73(s, 4H); 2.63(s, 3H); 2.38(s, 3H) |
| 3.29 | $CH_3$ | $CH_3$ | 4-methyl-3-chloro-phenyl | 7.19–8.08(m, 5H); 3.87(s, 3H); 3.72 (s, 3H); 2.63(s, 3H); 2.36(s, 3H); 2.30(s, 3H). |
| 3.30 | $CH_3$ | $CH_3$ | 3-cyanophenyl | 7.58–8.22(m, 6H); 3.91(s, 3H); 3.75(s, 3H); 2.63(s, 3H); 2.39(s, 3H). |
| 3.31 | $CH_3$ | $CH_3$ | 3-chlorophenyl | 7.25–8.17(m, 6H); 3.92(s, 3H); 3.74(s, 3H); 2.61(s, 3H); 2.39(s, 3H). |
| 3.32 | $CH_3$ | $CH_3$ | 3-fluorophenyl | 6.96–8.18(m, 6H); 3.91(s, 3H); 3.74(s, 3H); 2.62(s, 3H); 2.39(s, 3H). |
| 3.33 | $CH_3$ | $CH_3$ | 3-methoxyphenyl | 6.82–8.17(m, 6H); 3.92(s, 3H); 3.89(s, 3H); 3.75(s, 3H); 2.60(s, 3H); 2.38(s, 3H). |
| 3.34 | $CH_3$ | $OCH_3$ | 2-methylphenyl | 6.98–7.60(m, 6H); 3.96(s, 3H); 3.87(s, 3H); 3.70(s, 3H); 2.61(s, 3H); 2.18(s, 3H). |
| 3.35 | $CH_3$ | $OCH_3$ | 2,5-dichlorophenyl | 7.24–8.19(m, 5H); 3.98(s, 3H); 3.87(s, 3H); 3.73(s, 3H); 2.54(s, 3H). |

TABLE 3-continued

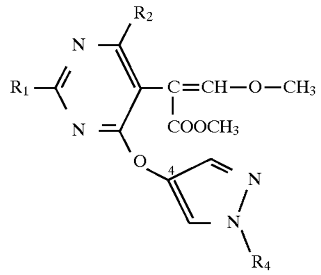

| Comp. No. | $R_1$ | $R_2$ | $R_4$ | physical data $^1H-NMR$ ($CDCl_3$) or/and m.p. |
|---|---|---|---|---|
| 3.36 | $CH_3$ | $CH_3$ | 2,4,5-trichloro-phenyl | 7.63–8.24(m, 4H); 3.91(s, 3H); 3.75(s, 3H); 2.61(s, 3H); 2.37(s, 3H). |
| 3.37 | $CH_3$ | $CH_3$ | 3-ethylphenyl | 7.11–8.16(m, 6H); 3.90(s, 3H); 3.74(s, 3H); 2.72(t, 2H); 2.62(s, 3H); 2.37(s, 3H); 1.28(t, 4H). |
| 3.38 | $CH_3$ | $CH_3$ | 2-benzylphenyl | 7.29–7.96(m, 11H); 4.02(s, 2H); 3.94(s, 3H); 3.76(s, 3H); 2.59(s, 3H); 2.38(s, 3H). |
| 3.39 | $CH_3$ | $CH_3$ | 2-phenoxyphenyl | 7.00–8.38(m, 11H); 3.85(s, 3H); 3.68(s, 3H); 2.49(s, 3H); 2.34(s, 3H). |
| 3.40 | $CH_3$ | $CH_3$ | 3,5-dimethylphenyl | 6.92–8.11(m, 5H); 3.91(s, 3H); 3.76(s, 3H); 2.62(s, 3H); 2.40(s, 6H); 2.38(s, 3H). |
| 3.41 | $CH_3$ | $CH_3$ | 1-naphthyl | 7.52–8.11(m, 9H); 3.93(s, 3H); 3.77(s, 3H); 2.62(s, 3H); 2.39(s, 3H). |

TABLE 4

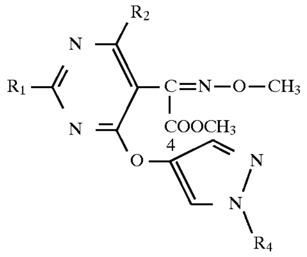

| Comp. No. | $R_1$ | $R_2$ | $R_4$ | physical data |
|---|---|---|---|---|
| 4.01 | $CH_3$ | $CH_3$ | 2,3-dichlorophenyl | |
| 4.02 | $CH_3$ | $CH_3$ | 2-chlorophenyl | |

TABLE 4-continued

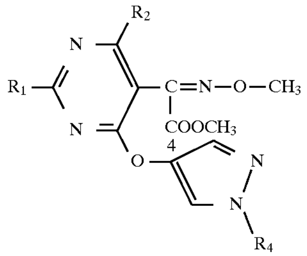

| Comp. No. | $R_1$ | $R_2$ | $R_4$ | physical data |
|---|---|---|---|---|
| 4.03 | $CH_3$ | $CH_3$ | 2,4-dichlorophenyl | |
| 4.04 | $CH_3$ | $CH_3$ | 2,5-dichlorophenyl | |
| 4.05 | $CH_3$ | $CH_3$ | 2,6-dichlorophenyl | |
| 4.06 | $CH_3$ | $CH_3$ | 2-methylphenyl | |
| 4.07 | $CH_3$ | $CH_3$ | 2-isopropylphenyl | |
| 4.08 | $CH_3$ | $CH_3$ | 2-$CF_3$-phenyl | |
| 4.09 | $CH_3$ | $CH_3$ | 2-methoxyphenyl | |
| 4.10 | $CH_3$ | $CH_3$ | 2-methyl-5-chlorophenyl | |
| 4.11 | $CH_3$ | $CH_3$ | phenyl | |
| 4.12 | $CH_3$ | $CH_3$ | 3-methylphenyl | |
| 4.13 | $CH_3$ | $CH_3$ | 2-chloro-4-methylphenyl | |
| 4.14 | $CH_3$ | $CH_3$ | 2-cyano-4-chlorophenyl | |
| 4.15 | $CH_3$ | $CH_3$ | 3-$CF_3$-phenyl | |
| 4.16 | $CH_3$ | $CH_3$ | 4-chlorophenyl | |
| 4.17 | $CH_3$ | $CH_3$ | 2-cyanophenyl | |
| 4.18 | $CH_3$ | $CH_3$ | 2-methyl-3-chlorophenyl | |
| 4.19 | $CH_3$ | $CH_3$ | 2-methyl-4-chlorophenyl | |
| 4.20 | $CH_3$ | $CH_3$ | 2,3-dimethylphenyl | |
| 4.21 | $CH_3$ | $CH_3$ | 2,6-dimethylphenyl | |
| 4.22 | $CH_3$ | $CH_3$ | 2-methyl-6-chlorophenyl | |
| 4.23 | $CH_3$ | $CH_3$ | 4-methylphenyl | |
| 4.24 | $CH_3$ | $CH_3$ | 2-ethylphenyl | |
| 4.25 | $CH_3$ | $CH_3$ | 2-fluorophenyl | |
| 4.26 | $CH_3$ | $CH_3$ | 2-biphenylyl | |
| 4.27 | $CH_3$ | $CH_3$ | 3,4-dichlorophenyl | |
| 4.28 | $CH_3$ | $CH_3$ | 3,5-dichlorophenyl | |
| 4.29 | $CH_3$ | $CH_3$ | 4-methyl-3-chloro-phenyl | |
| 4.30 | $CH_3$ | $CH_3$ | 3-cyanophenyl | |
| 4.31 | $CH_3$ | $CH_3$ | 3-chlorophenyl | |
| 4.32 | $CH_3$ | $CH_3$ | 3-fluorophenyl | |
| 4.33 | $CH_3$ | $CH_3$ | 3-methoxyphenyl | |
| 4.34 | $CH_3$ | $OCH_3$ | 2-methylphenyl | |
| 4.35 | $CH_3$ | $OCH_3$ | 2,5-dichlorophenyl | |
| 4.36 | $CH_3$ | $CH_3$ | 2,4,5-trichlorophenyl | |

TABLE 5

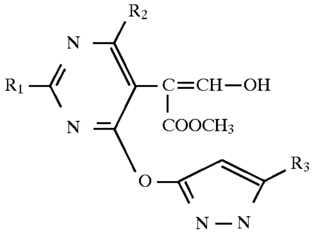

| Comp. No. | $R_1$ | $R_2$ | $R_3$ | $R_4$ | physical data |
|---|---|---|---|---|---|
| 5.01 | $CH_3$ | $CH_3$ | $CH_3$ | 2,3-dichlorophenyl | |
| 5.02 | $CH_3$ | $CH_3$ | $CH_3$ | 2-chlorophenyl | |
| 5.03 | $CH_3$ | $CH_3$ | $CH_3$ | 2,4-dichlorophenyl | |
| 5.04 | $CH_3$ | $CH_3$ | $CH_3$ | 2,5-dichlorophenyl | |
| 5.05 | $CH_3$ | $CH_3$ | $CH_3$ | 2,6-dichlorophenyl | |
| 5.06 | $CH_3$ | $CH_3$ | $CH_3$ | 2,4,5-trichlorophenyl | |
| 5.07 | $CH_3$ | $CH_3$ | $CH_3$ | 2,4,6-trichlorophenyl | |
| 5.08 | $CH_3$ | $CH_3$ | $CH_3$ | 2-$CF_3$-phenyl | |
| 5.09 | $CH_3$ | $CH_3$ | $CH_3$ | 2-fluorophenyl | |
| 5.10 | $CH_3$ | $CH_3$ | $CH_3$ | 2-methyl-5-chlorophenyl | |
| 5.11 | $CH_3$ | $CH_3$ | $CH_3$ | phenyl | |
| 5.12 | $CH_3$ | $CH_3$ | H | phenyl | |
| 5.13 | $CH_3$ | $CH_3$ | H | 2-chlorophenyl | |
| 5.14 | $CH_3$ | $CH_3$ | H | 2,4-dichlorophenyl | |
| 5.15 | $CH_3$ | $CH_3$ | H | 2-fluorophenyl | |
| 5.16 | $CH_3$ | $CH_3$ | H | benzyl | |
| 5.17 | $CH_3$ | $CH_3$ | H | 2,6-dichlorobenzyl | |
| 5.18 | $CH_3$ | $CH_3$ | H | 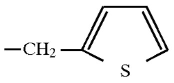 | |
| 5.19 | $CH_3$ | $CH_3$ | H | 3-methoxybenzyl | |
| 5.20 | $CH_3$ | $CH_3$ | H | 4-methoxybenzyl | |
| 5.21 | $CH_3$ | $N(CH_3)_2$ | H | phenyl | |
| 5.22 | $CH_3$ | $CH_3$ | $CH_3$ | 2-cyanophenyl | |
| 5.23 | $CH_3$ | $CH_3$ | $CH_3$ | 3-chlorophenyl | |
| 5.24 | $CH_3$ | $CH_3$ | $CH_3$ | 3-$CF_3$-phenyl | |
| 5.25 | $CH_3$ | $CH_3$ | $CH_3$ | 2-nitrophenyl | |
| 5.26 | $CH_3$ | $CH_3$ | $CH_3$ | 2-methoxy-5-chloro-phenyl | |
| 5.27 | $CH_3$ | $CH_3$ | H | 2-methylphenyl | |
| 5.28 | $CH_3$ | $CH_3$ | $CH_3$ | 3,4-dichlorophenyl | |
| 5.29 | $CH_3$ | $CH_3$ | $CH_3$ | 3-nitrophenyl | |
| 5.30 | $CH_3$ | $CH_3$ | $CH_3$ | 3-$CF_3$-4-chloro-phenyl | |
| 5.31 | $CH_3$ | $OCH_3$ | H | 2-chlorophenyl | |
| 5.32 | $CH_3$ | $OCH_3$ | $CH_3$ | 2-chlorophenyl | |
| 5.33 | $CH_3$ | $OCH_3$ | H | 2-methoxybenzyl | |
| 5.34 | $C_2H_5$ | $OCH_3$ | H | 2-methoxybenzyl | |
| 5.35 | $CH_3$ | $OCH_3$ | H | 2-chlorobenzyl | |
| 5.36 | $C_2H_5$ | $OCH_3$ | H | 2-chlorobenzyl | |
| 5.37 | $CH_3$ | $CH_3$ | H | 2-methoxybenzyl | |
| 5.38 | $CH_3$ | $CH_3$ | H | 2,5-dichlorophenyl | |
| 5.39 | $CH_3$ | $CH_3$ | H | 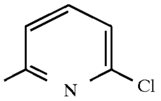 | |
| 5.40 | $CH_3$ | $CH_3$ | $CH_3$ | 3-methoxyphenyl | |
| 5.41 | $CH_3$ | $CH_3$ | H | 3-chlorophenyl | |
| 5.42 | $CH_3$ | $CH_3$ | $CH_3$ | 3,5-dichlorophenyl | |
| 5.43 | $CH_3$ | $SCH_3$ | H | 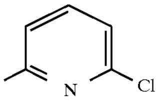 | |
| 5.44 | $CH_3$ | $OCH_3$ | H | 3-chlorophenyl | |

TABLE 5-continued

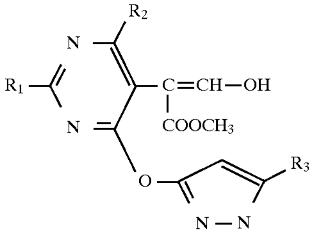

| Comp. No. | $R_1$ | $R_2$ | $R_3$ | $R_4$ | physical data |
|---|---|---|---|---|---|
| 5.45 | $CH_3$ | $OCH_3$ | H | 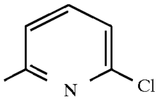 | |
| 5.46 | $CH_3$ | $CH_3$ | H | 3-cyanophenyl | |
| 5.47 | $CH_3$ | $CH_3$ | H | 4-biphenylyl | |
| 5.48 | $CH_3$ | $CH_3$ | H | 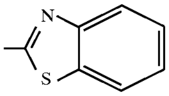 | |
| 5.49 | $CH_3$ | $CH_3$ | H | 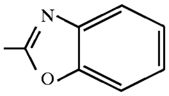 | |
| 5.50 | $CH_3$ | $CH_3$ | H | 3,4-dichlorophenyl | |
| 5.51 | $CH_3$ | $CH_3$ | H | 3-$CF_3$-phenyl | |
| 5.52 | $CH_3$ | $CH_3$ | H | 3-methoxyphenyl | |
| 5.53 | $CH_3$ | $CH_3$ | H | 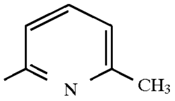 | |
| 5.54 | $CH_3$ | $CH_3$ | H | 2-nitrophenyl | |
| 5.55 | $CH_3$ | $CH_3$ | H | 3-nitrophenyl | |
| 5.56 | $CH_3$ | $CH_3$ | H | 2,6-dichlorophenyl | |
| 5.57 | $CH_3$ | $CH_3$ | $CH_3$ | 5-$CF_3$-2-chloro-phenyl | |
| 5.58 | $CH_3$ | $CH_3$ | $CH_3$ | 4-biphenylyl | |
| 5.59 | $CH_3$ | $CH_3$ | $CH_3$ | 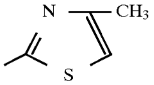 | |
| 5.60 | $CH_3$ | $CH_3$ | $CH_3$ | 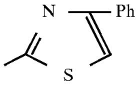 | |
| 5.61 | $CH_3$ | $CH_3$ | $CH_3$ | 3,4-dimethoxyphenyl | |
| 5.62 | $CH_3$ | $CH_3$ | $CH_3$ | 2-pyridyl | |
| 5.63 | $CH_3$ | $CH_3$ | $CH_3$ | 4-phenoxyphenyl | |
| 5.64 | $CH_3$ | $CH_3$ | H | 2-methyl-5-chloro-phenyl | |
| 5.65 | $CH_3$ | $CH_3$ | H | 4-chlorophenyl | |
| 5.66 | $CH_3$ | $CH_3$ | $CH_3$ | 3-fluorophenyl | |
| 5.67 | $CH_3$ | $CH_3$ | $CH_3$ | 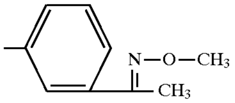 | |
| 5.68 | $CH_3$ | $CH_3$ | $CH_3$ | 4-fluorophenyl | |
| 5.69 | $CH_3$ | $CH_3$ | $CH_3$ | 4-chlorophenyl | |
| 5.70 | $CH_3$ | $OCH_3$ | H | 3,4-dichlorophenyl | |
| 5.71 | $CH_3$ | $OCH_3$ | $CH_3$ | 3-$CF_3$-phenyl | |
| 5.72 | $N(CH_3)_2$ | $CH_3$ | H | 3-chlorophenyl | |

TABLE 5-continued

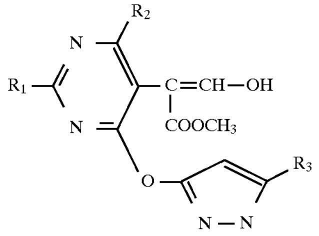

| Comp. No. | $R_1$ | $R_2$ | $R_3$ | $R_4$ | physical data |
|---|---|---|---|---|---|
| 5.73 | $CH_3$ | $CH_3$ | H | 3-$CF_3$-phenyl | |
| 5.74 | $CH_3$ | $OCH_3$ | H | 2,5-dichlorophenyl | |
| 5.75 | H | $CH_3$ | H | 3-$CF_3$-phenyl | |
| 5.76 | $CH_3$ | $OCH_3$ | H | 5-chloro-2-methylphenyl | |
| 5.77 | $CH_3$ | $CH_3$ | $CH_3$ | 3-chloro-2-methylphenyl | |
| 5.78 | $CH_3$ | $CH_3$ | $CH_3$ | 4-chloro-2-methylphenyl | |
| 5.79 | $CH_3$ | $OCH_3$ | $CH_3$ | 3-chlorophenyl | |
| 5.80 | $CH_3$ | $OCH_3$ | $CH_3$ | 4-chlorophenyl | |
| 5.81 | $CH_3$ | $OCH_3$ | $CH_3$ | 3,4-dichlorophenyl | |
| 5.82 | $CH_3$ | $OCH_3$ | $CH_3$ | 2,3-dichlorophenyl | |
| 5.83 | $CH_3$ | $OCH_3$ | $CH_3$ | 3,5-dichlorophenyl | |
| 5.84 | $CH_3$ | $OCH_3$ | $CH_3$ | 4-chloro-2-methylphenyl | |
| 5.85 | $CH_3$ | $OCH_3$ | $CH_3$ | 3-chloro-2-methylphenyl | |
| 5.86 | $CH_3$ | $OCH_3$ | $CH_3$ | 2,4-dichlorophenyl | |
| 5.87 | $CH_3$ | $OCH_3$ | $CH_3$ | 5-chloro-2-methylphenyl | |
| 5.88 | $CH_3$ | $CH_3$ | $CH_3$ | 3-bromophenyl | |
| 5.89 | $CH_3$ | $CH_3$ | $CH_3$ | 4-bromophenyl | |
| 5.90 | $CH_3$ | $OCH_3$ | $CH_3$ | 3-bromophenyl | |
| 5.91 | $CH_3$ | $OCH_3$ | H | 3-bromophenyl | |
| 5.92 | $CH_3$ | $OCH_3$ | H | 4-methylphenyl | |
| 5.93 | $CH_3$ | $CH_3$ | H | 4-bromophenyl | |
| 5.94 | $CH_3$ | $CH_3$ | H | 4-bromophenyl | |
| 5.95 | $CH_3$ | $CH_3$ | H | 3-bromophenyl | |
| 5.96 | $CH_3$ | $CH_3$ | H | 4-bromophenyl | |
| 5.97 | $CH_3$ | $CH_3$ | H | 4-methylphenyl | |
| 5.98 | $CH_3$ | $CH_3$ | H | 2,5-dimethylphenyl | |
| 5.99 | $CH_3$ | $CH_3$ | $CH_3$ | 3,5-dimethylphenyl | |

TABLE 6

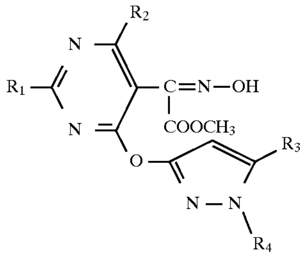

| Comp. No. | $R_1$ | $R_2$ | $R_3$ | $R_4$ | physical data |
|---|---|---|---|---|---|
| 6.01 | $CH_3$ | $CH_3$ | $CH_3$ | 2,3-dichlorophenyl | |
| 6.02 | $CH_3$ | $CH_3$ | $CH_3$ | 2-chlorophenyl | |
| 6.03 | $CH_3$ | $CH_3$ | $CH_3$ | 2,4-dichlorophenyl | |
| 6.04 | $CH_3$ | $CH_3$ | $CH_3$ | 2,5-dichlorophenyl | |
| 6.05 | $CH_3$ | $CH_3$ | $CH_3$ | 2,6-dichlorophenyl | |
| 6.06 | $CH_3$ | $CH_3$ | $CH_3$ | 2,4,5-trichlorophenyl | |
| 6.07 | $CH_3$ | $CH_3$ | $CH_3$ | 2,4,6-trichlorophenyl | |
| 6.08 | $CH_3$ | $CH_3$ | $CH_3$ | 2-$CF_3$-phenyl | |
| 6.09 | $CH_3$ | $CH_3$ | $CH_3$ | 2-fluorophenyl | |

TABLE 6-continued

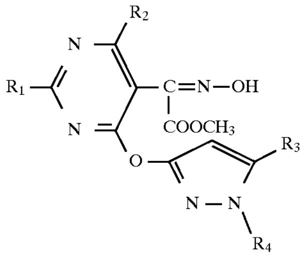

| Comp. No. | $R_1$ | $R_2$ | $R_3$ | $R_4$ | physical data |
|---|---|---|---|---|---|
| 6.10 | $CH_3$ | $CH_3$ | $CH_3$ | 2-methyl-5-chlorophenyl | |
| 6.11 | $CH_3$ | $CH_3$ | $CH_3$ | phenyl | |
| 6.12 | $CH_3$ | $CH_3$ | H | phenyl | |
| 6.13 | $CH_3$ | $CH_3$ | H | 2-chlorophenyl | |
| 6.14 | $CH_3$ | $CH_3$ | H | 2,4-dichlorophenyl | |
| 6.15 | $CH_3$ | $CH_3$ | H | 2-fluorophenyl | |
| 6.16 | $CH_3$ | $CH_3$ | H | benzyl | |
| 6.17 | $CH_3$ | $CH_3$ | H | 2,6-dichlorobenzyl | |

TABLE 6-continued

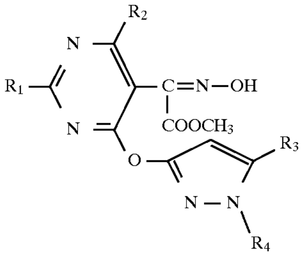

| Comp. No. | $R_1$ | $R_2$ | $R_3$ | $R_4$ | physical data |
|---|---|---|---|---|---|
| 6.18 | $CH_3$ | $CH_3$ | H | 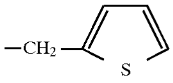 | |
| 6.19 | $CH_3$ | $CH_3$ | H | 3-methoxybenzyl | |
| 6.20 | $CH_3$ | $CH_3$ | H | 4-methoxybenzyl | |
| 6.21 | $CH_3$ | $N(CH_3)_2$ | H | phenyl | |
| 6.22 | $CH_3$ | $CH_3$ | $CH_3$ | 2-cyanophenyl | |
| 6.23 | $CH_3$ | $CH_3$ | $CH_3$ | 3-chlorophenyl | |
| 6.24 | $CH_3$ | $CH_3$ | $CH_3$ | 3-$CF_3$-phenyl | |
| 6.25 | $CH_3$ | $CH_3$ | $CH_3$ | 2-nitrophenyl | |
| 6.26 | $CH_3$ | $CH_3$ | $CH_3$ | 2-methoxy-5-chloro-phenyl | |
| 6.27 | $CH_3$ | $CH_3$ | H | 2-methylphenyl | |
| 6.28 | $CH_3$ | $CH_3$ | $CH_3$ | 3,4-dichlorophenyl | |
| 6.29 | $CH_3$ | $CH_3$ | $CH_3$ | 3-nitrophenyl | |
| 6.30 | $CH_3$ | $CH_3$ | $CH_3$ | 3-$CF_3$-4-chloro-phenyl | |
| 6.31 | $CH_3$ | $OCH_3$ | H | 2-chlorophenyl | |
| 6.32 | $CH_3$ | $OCH_3$ | $CH_3$ | 2-chlorophenyl | |
| 6.33 | $CH_3$ | $OCH_3$ | H | 2-methoxybenzyl | |
| 6.34 | $C_2H_5$ | $OCH_3$ | H | 2-methoxybenzyl | |
| 6.35 | $CH_3$ | $OCH_3$ | H | 2-chlorobenzyl | |
| 6.36 | $C_2H_5$ | $OCH_3$ | H | 2-chlorobenzyl | |
| 6.37 | $CH_3$ | $CH_3$ | H | 2-methoxybenzyl | |
| 6.38 | $CH_3$ | $CH_3$ | H | 2,5-dichlorophenyl | |
| 6.39 | $CH_3$ | $CH_3$ | H | 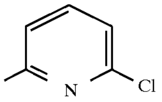 | |
| 6.40 | $CH_3$ | $CH_3$ | $CH_3$ | 3-methoxyphenyl | |
| 6.41 | $CH_3$ | $CH_3$ | H | 3-chlorophenyl | |
| 6.42 | $CH_3$ | $CH_3$ | $CH_3$ | 3,5-dichlorophenyl | |
| 6.43 | $CH_3$ | $SCH_3$ | H | 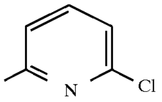 | |
| 6.44 | $CH_3$ | $OCH_3$ | H | 3-chlorophenyl | |
| 6.45 | $CH_3$ | $OCH_3$ | H | 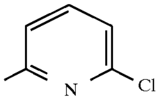 | |
| 6.46 | $CH_3$ | $CH_3$ | H | 3-cyanophenyl | |
| 6.47 | $CH_3$ | $CH_3$ | H | 4-biphenylyl | |
| 6.48 | $CH_3$ | $CH_3$ | H | 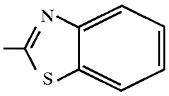 | |

TABLE 6-continued

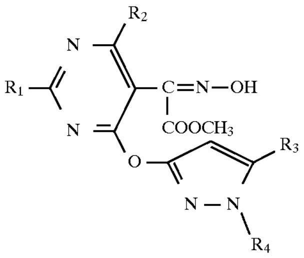

| Comp. No. | $R_1$ | $R_2$ | $R_3$ | $R_4$ | physical data |
|---|---|---|---|---|---|
| 6.49 | $CH_3$ | $CH_3$ | H | 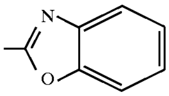 | |
| 6.50 | $CH_3$ | $CH_3$ | H | 3,4-dichlorophenyl | |
| 6.51 | $CH_3$ | $CH_3$ | H | 3-$CF_3$-phenyl | |
| 6.52 | $CH_3$ | $CH_3$ | H | 3-methoxyphenyl | |
| 6.53 | $CH_3$ | $CH_3$ | H | 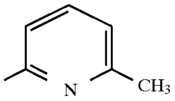 | |
| 6.54 | $CH_3$ | $CH_3$ | H | 2-nitrophenyl | |
| 6.55 | $CH_3$ | $CH_3$ | H | 3-nitrophenyl | |
| 6.56 | $CH_3$ | $CH_3$ | H | 2,6-dichlorophenyl | |
| 6.57 | $CH_3$ | $CH_3$ | $CH_3$ | 5-$CF_3$-2-chloro-phenyl | |
| 6.58 | $CH_3$ | $CH_3$ | $CH_3$ | 4-biphenylyl | |
| 6.59 | $CH_3$ | $CH_3$ | $CH_3$ | 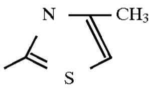 | |
| 6.60 | $CH_3$ | $CH_3$ | $CH_3$ | 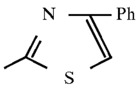 | |
| 6.61 | $CH_3$ | $CH_3$ | $CH_3$ | 3,4-dimethoxyphenyl | |

TABLE 7

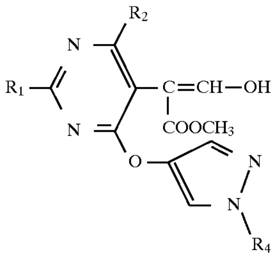

| Comp. No. | $R_1$ | $R_2$ | $R_4$ | physical data |
|---|---|---|---|---|
| 7.01 | $CH_3$ | $CH_3$ | 2,3-dichlorophenyl | |
| 7.02 | $CH_3$ | $CH_3$ | 2-chlorophenyl | |
| 7.03 | $CH_3$ | $CH_3$ | 2,4-dichlorophenyl | |
| 7.04 | $CH_3$ | $CH_3$ | 2,5-dichlorophenyl | |
| 7.05 | $CH_3$ | $CH_3$ | 2,6-dichlorophenyl | |
| 7.06 | $CH_3$ | $CH_3$ | 2-methylphenyl | |
| 7.07 | $CH_3$ | $CH_3$ | 2-isopropylphenyl | |
| 7.08 | $CH_3$ | $CH_3$ | 2-$CF_3$-phenyl | |
| 7.09 | $CH_3$ | $CH_3$ | 2-methoxyphenyl | |

TABLE 7-continued

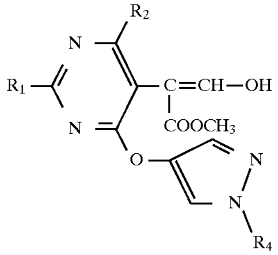

| Comp. No. | $R_1$ | $R_2$ | $R_4$ | physical data |
|---|---|---|---|---|
| 7.10 | $CH_3$ | $CH_3$ | 2-methyl-5-chlorophenyl | |
| 7.11 | $CH_3$ | $CH_3$ | phenyl | |
| 7.12 | $CH_3$ | $CH_3$ | 3-methylphenyl | |
| 7.13 | $CH_3$ | $CH_3$ | 2-chloro-4-methylphenyl | |
| 7.14 | $CH_3$ | $CH_3$ | 2-cyano-4-chlorophenyl | |
| 7.15 | $CH_3$ | $CH_3$ | 3-$CF_3$-phenyl | |
| 7.16 | $CH_3$ | $CH_3$ | 4-chlorophenyl | |
| 7.17 | $CH_3$ | $CH_3$ | 2-cyanophenyl | |
| 7.18 | $CH_3$ | $CH_3$ | 2-methyl-3-chlorophenyl | |
| 7.19 | $CH_3$ | $CH_3$ | 2-methyl-4-chlorophenyl | |
| 7.20 | $CH_3$ | $CH_3$ | 2,3-dimethylphenyl | |
| 7.21 | $CH_3$ | $CH_3$ | 2,6-dimethylphenyl | |
| 7.22 | $CH_3$ | $CH_3$ | 2-methyl-6-chlorophenyl | |
| 7.23 | $CH_3$ | $CH_3$ | 4-methylphenyl | |
| 7.24 | $CH_3$ | $CH_3$ | 2-ethylphenyl | |
| 7.25 | $CH_3$ | $CH_3$ | 2-fluorophenyl | |
| 7.26 | $CH_3$ | $CH_3$ | 2-biphenylyl | |
| 7.27 | $CH_3$ | $CH_3$ | 3,4-dichlorophenyl | |
| 7.28 | $CH_3$ | $CH_3$ | 3,5-dichlorophenyl | |
| 7.29 | $CH_3$ | $CH_3$ | 4-methyl-3-chloro-phenyl | |
| 7.30 | $CH_3$ | $CH_3$ | 3-cyanophenyl | |
| 7.31 | $CH_3$ | $CH_3$ | 3-chlorophenyl | |
| 7.32 | $CH_3$ | $CH_3$ | 3-fluorophenyl | |
| 7.33 | $CH_3$ | $CH_3$ | 3-methoxyphenyl | |
| 7.34 | $CH_3$ | $OCH_3$ | 2-methylphenyl | |
| 7.35 | $CH_3$ | $OCH_3$ | 2,5-dichlorophenyl | |
| 7.36 | $CH_3$ | $CH_3$ | 2,4,5-trichlorophenyl | |

TABLE 8

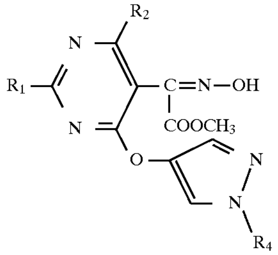

| Comp. No. | $R_1$ | $R_2$ | $R_4$ | physical data |
|---|---|---|---|---|
| 8.01 | $CH_3$ | $CH_3$ | 2,3-dichlorophenyl | |
| 8.02 | $CH_3$ | $CH_3$ | 2-chlorophenyl | |
| 8.03 | $CH_3$ | $CH_3$ | 2,4-dichlorophenyl | |
| 8.04 | $CH_3$ | $CH_3$ | 2,5-dichlorophenyl | |
| 8.05 | $CH_3$ | $CH_3$ | 2,6-dichlorophenyl | |
| 8.06 | $CH_3$ | $CH_3$ | 2-methylphenyl | |

TABLE 8-continued

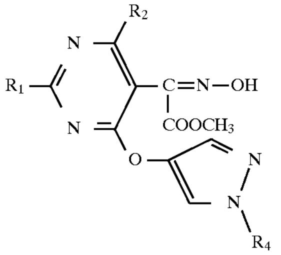

| Comp. No. | $R_1$ | $R_2$ | $R_4$ | physical data |
|---|---|---|---|---|
| 8.07 | $CH_3$ | $CH_3$ | 2-isopropylphenyl | |
| 8.08 | $CH_3$ | $CH_3$ | 2-$CF_3$-phenyl | |
| 8.09 | $CH_3$ | $CH_3$ | 2-methoxyphenyl | |
| 8.10 | $CH_3$ | $CH_3$ | 2-methyl-5-chlorophenyl | |
| 8.11 | $CH_3$ | $CH_3$ | phenyl | |
| 8.12 | $CH_3$ | $CH_3$ | 3-methylphenyl | |
| 8.13 | $CH_3$ | $CH_3$ | 2-chloro-4-methylphenyl | |
| 8.14 | $CH_3$ | $CH_3$ | 2-cyano-4-chlorophenyl | |
| 8.15 | $CH_3$ | $CH_3$ | 3-$CF_3$-phenyl | |
| 8.16 | $CH_3$ | $CH_3$ | 4-chlorophenyl | |
| 8.17 | $CH_3$ | $CH_3$ | 2-cyanophenyl | |
| 8.18 | $CH_3$ | $CH_3$ | 2-methyl-3-chlorophenyl | |
| 8.19 | $CH_3$ | $CH_3$ | 2-methyl-4-chlorophenyl | |
| 8.20 | $CH_3$ | $CH_3$ | 2,3-dimethylphenyl | |
| 8.21 | $CH_3$ | $CH_3$ | 2,6-dimethylphenyl | |
| 8.22 | $CH_3$ | $CH_3$ | 2-methyl-6-chlorophenyl | |
| 8.23 | $CH_3$ | $CH_3$ | 4-methylphenyl | |
| 8.24 | $CH_3$ | $CH_3$ | 2-ethylphenyl | |
| 8.25 | $CH_3$ | $CH_3$ | 2-fluorophenyl | |
| 8.26 | $CH_3$ | $CH_3$ | 2-biphenylyl | |
| 8.27 | $CH_3$ | $CH_3$ | 3,4-dichlorophenyl | |
| 8.28 | $CH_3$ | $CH_3$ | 3,5-dichlorophenyl | |
| 8.29 | $CH_3$ | $CH_3$ | 4-methyl-3-chloro-phenyl | |
| 8.30 | $CH_3$ | $CH_3$ | 3-cyanophenyl | |
| 8.31 | $CH_3$ | $CH_3$ | 3-chlorophenyl | |
| 8.32 | $CH_3$ | $CH_3$ | 3-fluorophenyl | |
| 8.33 | $CH_3$ | $CH_3$ | 3-methoxyphenyl | |
| 8.34 | $CH_3$ | $OCH_3$ | 2-methylphenyl | |
| 8.35 | $CH_3$ | $OCH_3$ | 2,5-dichlorophenyl | |
| 8.36 | $CH_3$ | $CH_3$ | 2,4,5-trichlorophenyl | |

TABLE 9

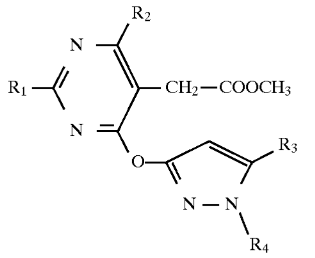

| Comp. No. | $R_1$ | $R_2$ | $R_3$ | $R_4$ | physical data |
| --- | --- | --- | --- | --- | --- |
| 9.01 | $CH_3$ | $CH_3$ | $CH_3$ | 2,3-dichlorophenyl | |
| 9.02 | $CH_3$ | $CH_3$ | $CH_3$ | 2-chlorophenyl | |
| 9.03 | $CH_3$ | $CH_3$ | $CH_3$ | 2,4-dichlorophenyl | |
| 9.04 | $CH_3$ | $CH_3$ | $CH_3$ | 2,5-dichlorophenyl | |
| 9.05 | $CH_3$ | $CH_3$ | $CH_3$ | 2,6-dichlorophenyl | |
| 9.06 | $CH_3$ | $CH_3$ | $CH_3$ | 2,4,5-trichlorophenyl | |
| 9.07 | $CH_3$ | $CH_3$ | $CH_3$ | 2,4,6-trichlorophenyl | |
| 9.08 | $CH_3$ | $CH_3$ | $CH_3$ | 2-$CF_3$-phenyl | |
| 9.09 | $CH_3$ | $CH_3$ | $CH_3$ | 2-fluorophenyl | |
| 9.10 | $CH_3$ | $CH_3$ | $CH_3$ | 2-methyl-5-chlorophenyl | |
| 9.11 | $CH_3$ | $CH_3$ | $CH_3$ | phenyl | |
| 9.12 | $CH_3$ | $CH_3$ | H | phenyl | |
| 9.13 | $CH_3$ | $CH_3$ | H | 2-chlorophenyl | |
| 9.14 | $CH_3$ | $CH_3$ | H | 2,4-dichlorophenyl | |
| 9.15 | $CH_3$ | $CH_3$ | H | 2-fluorophenyl | |
| 9.16 | $CH_3$ | $CH_3$ | H | benzyl | |
| 9.17 | $CH_3$ | $CH_3$ | H | 2,6-dichlorobenzyl | |
| 9.18 | $CH_3$ | $CH_3$ | H | 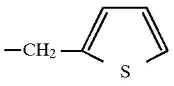 | |
| 9.19 | $CH_3$ | $CH_3$ | H | 3-methoxybenzyl | |
| 9.20 | $CH_3$ | $CH_3$ | H | 4-methoxybenzyl | |
| 9.21 | $CH_3$ | $N(CH_3)_2$ | H | phenyl | |
| 9.22 | $CH_3$ | $CH_3$ | $CH_3$ | 2-cyanophenyl | |
| 9.23 | $CH_3$ | $CH_3$ | $CH_3$ | 3-chlorophenyl | |
| 9.24 | $CH_3$ | $CH_3$ | $CH_3$ | 3-$CF_3$-phenyl | |
| 9.25 | $CH_3$ | $CH_3$ | $CH_3$ | 2-nitrophenyl | |
| 9.26 | $CH_3$ | $CH_3$ | $CH_3$ | 2-methoxy-5-chloro-phenyl | |
| 9.27 | $CH_3$ | $CH_3$ | H | 2-methylphenyl | |
| 9.28 | $CH_3$ | $CH_3$ | $CH_3$ | 3,4-dichlorophenyl | |
| 9.29 | $CH_3$ | $CH_3$ | $CH_3$ | 3-nitrophenyl | |
| 9.30 | $CH_3$ | $CH_3$ | $CH_3$ | 3-$CF_3$-4-chloro-phenyl | |
| 9.31 | $CH_3$ | $OCH_3$ | H | 2-chlorophenyl | |
| 9.32 | $CH_3$ | $OCH_3$ | $CH_3$ | 2-chlorophenyl | |
| 9.33 | $CH_3$ | $OCH_3$ | H | 2-methoxybenzyl | |
| 9.34 | $C_2H_5$ | $OCH_3$ | H | 2-methoxybenzyl | |
| 9.35 | $CH_3$ | $OCH_3$ | H | 2-chlorobenzyl | |
| 9.36 | $C_2H_5$ | $OCH_3$ | H | 2-chlorobenzyl | |
| 9.37 | $CH_3$ | $CH_3$ | H | 2-methoxybenzyl | |
| 9.38 | $CH_3$ | $CH_3$ | H | 2,5-dichlorophenyl | |
| 9.39 | $CH_3$ | $CH_3$ | H | 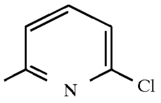 | |
| 9.40 | $CH_3$ | $CH_3$ | $CH_3$ | 3-methoxyphenyl | |
| 9.41 | $CH_3$ | $CH_3$ | H | 3-chlorophenyl | |
| 9.42 | $CH_3$ | $CH_3$ | $CH_3$ | 3,5-dichlorophenyl | |
| 9.43 | $CH_3$ | $SCH_3$ | H | 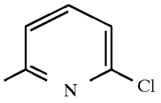 | |

TABLE 9-continued

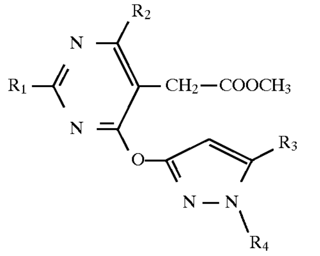

| Comp. No. | $R_1$ | $R_2$ | $R_3$ | $R_4$ | physical data |
|---|---|---|---|---|---|
| 9.44 | $CH_3$ | $OCH_3$ | H | 3-chlorophenyl | |
| 9.45 | $CH_3$ | $OCH_3$ | H | 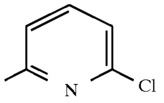 | |
| 9.46 | $CH_3$ | $CH_3$ | H | 3-cyanophenyl | |
| 9.47 | $CH_3$ | $CH_3$ | H | 4-biphenylyl | |
| 9.48 | $CH_3$ | $CH_3$ | H | 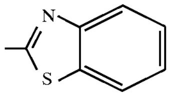 | |
| 9.49 | $CH_3$ | $CH_3$ | H | 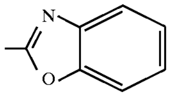 | |
| 9.50 | $CH_3$ | $CH_3$ | H | 3,4-dichlorophenyl | |
| 9.51 | $CH_3$ | $CH_3$ | H | 3-$CF_3$-phenyl | |
| 9.52 | $CH_3$ | $CH_3$ | H | 3-methoxyphenyl | |
| 9.53 | $CH_3$ | $CH_3$ | H | 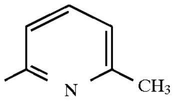 | |
| 9.54 | $CH_3$ | $CH_3$ | H | 2-nitrophenyl | |
| 9.55 | $CH_3$ | $CH_3$ | H | 3-nitrophenyl | |
| 9.56 | $CH_3$ | $CH_3$ | H | 2,6-dichlorophenyl | |
| 9.57 | $CH_3$ | $CH_3$ | $CH_3$ | 5-$CF_3$-2-chloro-phenyl | |
| 9.58 | $CH_3$ | $CH_3$ | $CH_3$ | 4-biphenylyl | |
| 9.59 | $CH_3$ | $CH_3$ | $CH_3$ | 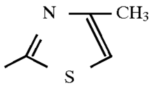 | |
| 9.60 | $CH_3$ | $CH_3$ | $CH_3$ | 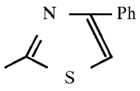 | |
| 9.61 | $CH_3$ | $CH_3$ | $CH_3$ | 3,4-dimethoxyphenyl | |
| 9.62 | $CH_3$ | $CH_3$ | $CH_3$ | 2-pyridyl | |
| 9.63 | $CH_3$ | $CH_3$ | $CH_3$ | 4-phenoxyphenyl | |
| 9.64 | $CH_3$ | $CH_3$ | H | 2-methyl-5-chloro-phenyl | |
| 9.65 | $CH_3$ | $CH_3$ | H | 4-chlorophenyl | |
| 9.66 | $CH_3$ | $CH_3$ | $CH_3$ | 3-fluorophenyl | |
| 9.67 | $CH_3$ | $CH_3$ | $CH_3$ | 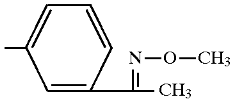 | |

TABLE 9-continued

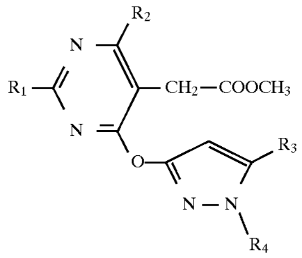

| Comp. No. | $R_1$ | $R_2$ | $R_3$ | $R_4$ | physical data |
|---|---|---|---|---|---|
| 9.68 | $CH_3$ | $CH_3$ | $CH_3$ | 4-fluorophenyl | |
| 9.69 | $CH_3$ | $CH_3$ | $CH_3$ | 4-chlorophenyl | |
| 9.70 | $CH_3$ | $OCH_3$ | H | 3,4-dichlorophenyl | |
| 9.71 | $CH_3$ | $OCH_3$ | $CH_3$ | 3-$CF_3$-phenyl | |
| 9.72 | $N(CH_3)_2$ | $CH_3$ | H | 3-chlorophenyl | |
| 9.73 | $CH_3$ | $OCH_3$ | H | 3-$CF_3$-phenyl | |
| 9.74 | $CH_3$ | $OCH_3$ | H | 2,5-dichlorophenyl | |
| 9.75 | H | $CH_3$ | H | 3-$CF_3$-phenyl | |
| 9.76 | $CH_3$ | $OCH_3$ | H | 5-chloro-2-methylphenyl | |
| 9.77 | $CH_3$ | $CH_3$ | $CH_3$ | 3-chloro-2-methylphenyl | |
| 9.78 | $CH_3$ | $CH_3$ | $CH_3$ | 4-chloro-2-methylphenyl | |
| 9.79 | $CH_3$ | $OCH_3$ | $CH_3$ | 3-chlorophenyl | |
| 9.80 | $CH_3$ | $OCH_3$ | $CH_3$ | 4-chlorophenyl | |
| 9.81 | $CH_3$ | $OCH_3$ | $CH_3$ | 3,4-dichlorophenyl | |
| 9.82 | $CH_3$ | $OCH_3$ | $CH_3$ | 2,3-dichlorophenyl | |
| 9.83 | $CH_3$ | $OCH_3$ | $CH_3$ | 3,5-dichlorophenyl | |
| 9.83 | $CH_3$ | $OCH_3$ | $CH_3$ | 2,4-dichlorophenyl | |
| 9.84 | $CH_3$ | $OCH_3$ | $CH_3$ | 4-chloro-2-methylphenyl | |
| 9.85 | $CH_3$ | $OCH_3$ | $CH_3$ | 3-chloro-2-methylphenyl | |
| 9.86 | $CH_3$ | $OCH_3$ | $CH_3$ | 2,4-dichlorophenyl | |
| 9.87 | $CH_3$ | $OCH_3$ | $CH_3$ | 5-chloro-2-methylphenyl | |
| 9.88 | $CH_3$ | $CH_3$ | $CH_3$ | 3-bromophenyl | |
| 9.89 | $CH_3$ | $CH_3$ | $CH_3$ | 4-bromophenyl | |
| 9.90 | $CH_3$ | $OCH_3$ | $CH_3$ | 3-bromophenyl | |
| 9.91 | $CH_3$ | $OCH_3$ | H | 3-bromophenyl | |
| 9.92 | $CH_3$ | $OCH_3$ | H | 4-methylphenyl | |
| 9.93 | $CH_3$ | $CH_3$ | H | 4-bromophenyl | |
| 9.94 | $CH_3$ | $OCH_3$ | H | 2,5-dimethylphenyl | |
| 9.95 | $CH_3$ | $CH_3$ | H | 3-bromophenyl | |
| 9.96 | $CH_3$ | $CH_3$ | H | 4-bromophenyl | |
| 9.97 | $CH_3$ | $CH_3$ | H | 4-bromophenyl | |
| 9.98 | $CH_3$ | $CH_3$ | H | 2,5-dimethylphenyl | |
| 9.99 | $CH_3$ | $CH_3$ | $CH_3$ | 3,5-dimethylphenyl | |

TABLE 10

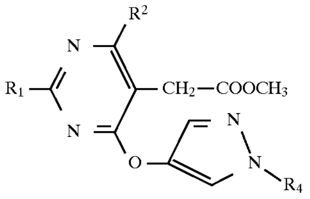

| Comp. No. | $R_1$ | $R_2$ | $R_4$ | physical data |
|---|---|---|---|---|
| 10.01 | $CH_3$ | $CH_3$ | 2,3-dichlorophenyl | |
| 10.02 | $CH_3$ | $CH_3$ | 2-chlorophenyl | |
| 10.03 | $CH_3$ | $CH_3$ | 2,4-dichlorophenyl | |
| 10.04 | $CH_3$ | $CH_3$ | 2,5-dichlorophenyl | |
| 10.05 | $CH_3$ | $CH_3$ | 2,6-dichlorophenyl | |

TABLE 10-continued

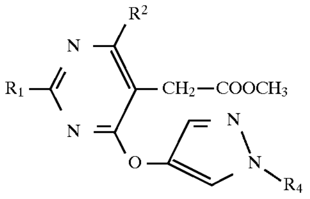

| Comp. No. | $R_1$ | $R_2$ | $R_4$ | physical data |
|---|---|---|---|---|
| 10.06 | $CH_3$ | $CH_3$ | 2,4,5-trichlorophenyl | |
| 10.07 | $CH_3$ | $CH_3$ | 2,4,6-trichlorophenyl | |
| 10.08 | $CH_3$ | $CH_3$ | 2-$CF_3$-phenyl | |
| 10.09 | $CH_3$ | $CH_3$ | 2-fluorophenyl | |
| 10.10 | $CH_3$ | $CH_3$ | 2-methyl-5- | |

TABLE 10-continued

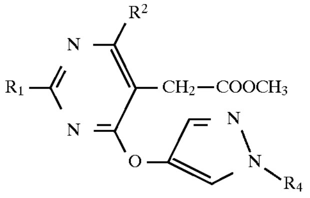

| Comp. No. | $R_1$ | $R_2$ | $R_4$ | physical data |
|---|---|---|---|---|
| | | | chlorophenyl | |
| 10.11 | $CH_3$ | $CH_3$ | phenyl | |
| 10.12 | $CH_3$ | $N(CH_3)_2$ | phenyl | |
| 10.13 | $CH_3$ | $CH_3$ | 2-cyanophenyl | |
| 10.14 | $CH_3$ | $CH_3$ | 2-chlorophenyl | |
| 10.15 | $CH_3$ | $CH_3$ | 3-$CF_3$-phenyl | |
| 10.16 | $CH_3$ | $CH_3$ | 2-nitrophenyl | |
| 10.17 | $CH_3$ | $CH_3$ | 2-methoxy-5-chloro-phenyl | |
| 10.18 | $CH_3$ | $CH_3$ | 2-methylphenyl | |
| 10.19 | $CH_3$ | $CH_3$ | 3,4-dichlorophenyl | |
| 10.20 | $CH_3$ | $CH_3$ | 3-nitrophenyl | |
| 10.21 | $CH_3$ | $CH_3$ | 3-$CF_3$-chloro-phenyl | |
| 10.22 | $OCH_3$ | $CH_3$ | 2-chlorophenyl | |

TABLE 11

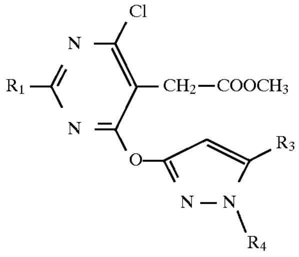

| Comp. No. | $R_1$ | $R_3$ | $R_4$ | physical data |
|---|---|---|---|---|
| 11.01 | $CH_3$ | $CH_3$ | phenyl | |
| 11.02 | $CH_3$ | H | phenyl | |
| 11.03 | $CH_3$ | H | 2-chlorophenyl | |
| 11.04 | $CH_3$ | $CH_3$ | 2-chlorophenyl | |
| 11.05 | $CH_3$ | H | 2-methoxybenzyl | |
| 11.06 | $C_2H_5$ | H | 2-methoxybenzyl | |
| 11.07 | $C_2H_5$ | H | 2-chlorobenzyl | |
| 11.08 | $CH_3$ | H | 2-chlorobenzyl | |
| 11.09 | $CH_3$ | H | 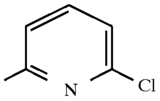 | |

TABLE 12

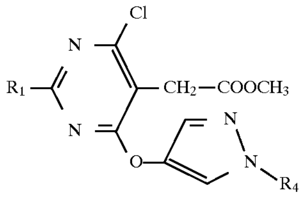

| Comp. No. | $R_1$ | $R_4$ | physical data |
|---|---|---|---|
| 12.01 | $CH_3$ | phenyl | |
| 12.02 | $CH_3$ | 2-methylphenyl | |
| 12.03 | $CH_3$ | 2,5-dichlorophenyl | |

EXAMPLE A

Activity Against Powdery Mildew

*Sphaeorotheca fuliginea*

Plants of Cucumis sativus (cucumber), 7 days old (cotyledon stage), are sprayed to near run off with a suspension containing 63 mg/l of active ingredient. The deposit is then allowed to dry. One day later, the treated plants are inoculated with a spore suspension containing $1\times10^5$/ml of freshly collected conidia of *Sphaeorotheca_fuliginea* and then incubated in the green house for 7 days at +24° C. and 60% r.h.

The efficacy of the test compounds is determined by comparing the degree of fungal attack with that on untreated similarly inoculated check plants. In this test compounds 1.03, 1.06, 1.09, 1.10, 1.12, 1.13, 1.38, 1.39, 1.40, 1.41, 1.43, 1.44, 1.45, 1.48, 1.51, 1.64, 1.65, 1.66, 1.67, 1.68, 1.69, 1.70, 1.71, 1.73, 1.74, 1.75, 1.76, 1.78, 1.79, 1.80, 1.81, 1.83, 1.86, 1.88, 1.89, 190, 1.92, 1.93, 1.94, 1.95, 1.96, 1.97, 1.98, 3.01, 3.02, 3.03, 3.04, 3.07, 3.08, 3.15, 3.16, 3.31, 3.35, 3.36, 3.37, 3.39, 3.40, 3.41 showed an efficacy of more than 90%.

Similar methods are used to test the compounds against the following pathogens:

*Podosphaera luecotricha* on apple,

*Erysiphe graminis* on wheat and barley (dry inoculation),

*Uncinula necator* on grape.

EXAMPLE B

Activity Against Rust, Scab, Pyrenophora, Leptosphaeria

*Uromyces appendiculatus*

Plants of Phaseolus vulgaris (pole bean), 14 days old (2 leaves stage), are sprayed to near run off with a suspension containing 63 mg/l of the active ingredient. The deposit is then allowed to dry. One day later, the treated plants are inoculated with a spore suspension containing $1\times10^5$/ml of freshly collected spores of *Uromyces_appendiculatus*. Incubation is performed for 3 days in a high humidity cabinet at +23° C. and >95% r.h. and thereafter during 10 days at +24° C. and 60% r.h.

The efficacy the compounds is determined by comparing the degree of fungal attack with that on untreated, similarly inoculated check plants. In this test compounds 1.01, 1.02, 1.03, 1.04, 1.06, 1.08, 1.09, 1.10, 1.11, 1.12, 1.13, 1.17, 1.37, 1.38, 1.39, 1.40, 1.41, 1.43, 1.44, 1.45, 1.48, 1.51, 1.64, 1.65, 1.66, 1.67, 1.68, 1.69, 1.70, 1.71, 1.73, 1.74, 1.75, 1.76, 1.77, 1.78, 1.79, 1.80, 1.81, 1.83, 1.84, 1.86, 1.88, 1.89, 1.90, 1.92, 1.93, 1.94, 1.95, 1.96, 1.97, 1.98, 1.99, 3.01, 3.02, 3.03, 3.04, 3.06, 3.07, 3.08, 3.09, 3.15, 3.16, 3.25, 3.31, 3.33, 3.35, 3.37, 3.38, 3.39, 3.40 and 3.41 showed an efficacy of at least 90%.

Similar methods are used to test the compounds against the following pathogens:

*Puccinia triticina* on wheat (plants 10 days old),

*Pyrenophora graminea* on barley,

*Leptosphaeria nodorum* on wheat,

*Venturia inaequalis* on apple (plants 21 days old; the spore suspension contains 1% malt).

EXAMPLE C

Activity against Downy Mildew

Plants of *Lycopersicon esculentum* (tomato) with 6 leaves, are sprayed to near run off with a spray suspension containing 63 mg/l of the active ingredient. The deposit is then allowed to dry. 1 day later, the treated plants are inoculated with a spore suspension containing $1\times10^5$/ml of freshly collected sporangia of Phytophthora infestans and then incubated for 7 days in a high humidity cabinet at +18° C. and >95% r.h. The efficacy of the test compounds is determined by comparing the degree of fungal attack with that on untreated, similarly inoculated check plants. In this test compounds 1.02, 1.03, 1.04, 1.06, 1.09, 1.10, 1.12, 1.17, 1.37, 1.38, 1.40, 1.41, 1.51, 1.65, 1.67, 1.69, 1.71, 1.73, 1.76, 1.78, 1.93, 1.95, 1.96, 1.97, 1.98, 3.01, 3.05, 3.06, 3.09, 3.40 and 3.41 showed efficacy of at least 90%.

A similar method is used to test the compounds against *Plasmopara viticola* on grape vine.

EXAMPLE D

Activity After Seed Treatment

The compounds of the invention may also be used for seed treatment. The advantageous fungicidal activity is established by in vitro tests with the following pathogens:

*Pyrenophora graminea,*

*Ustilago nuda,*

*Gerlachia nivalis,*

*Leptoshpaeria nodorum,*

Autoclaved wheat seeds are inoculated with spores or mycelium of the pathogens and coated with different concentration of the test compounds resulting in dosages of 50 g a.i./100 kg seed. The treated seeds are then placed on agar plates and the pathogens allowed to grow for 3–8 days at +24° C. in the dark.

The efficacy of the test compounds is determined by comparing the degree of fungal growth emerging from treated and untreated inoculated seeds.

To evaluate the crop plant tolerance of the compounds, healthy seeds of wheat and barley are coated with the dosages mentioned above. The seeds are then allowed to germinate in petri dishes on moist filter paper in high humidity at +18° C. for 10 days. Plant damage is recorded, comparing the growth of treated and untreated seedlings.

In this test compounds of formula I showed an efficacy of at least 90% against *Pyrenophora graminea.*

We claim:

1. A compound of formula I

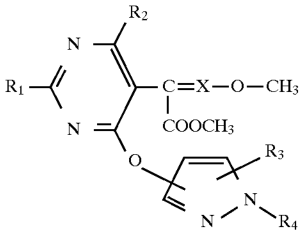

(I)

wherein $R_1$ is hydrogen, $C_{1-4}$ alkyl, $C_{1-4}$ alkoxy, $C_{3-6}$ cycloalkyl, $C_{1-4}$ alkylthio, or di- $C_{1-4}$ alkylamino, $R_2$ is hydrogen, $C_{1-4}$ alkyl, $C_{1-4}$ alkoxy, $C_{1-4}$ alkylthio, or di- $C_{1-4}$ alkylamino, $R_3$ is hydrogen or methyl, $R_4$ is phenyl, naphthyl, benzyl, phenyethyl, phenylpropyl, 1-phenylethyl, or a heteroaryl selected from the group consisting of pyridyl, pyrimidinyl, thienyl, oxazolyl, oxadiazolyl, triazolyl, thiadiazolyl, furyl, isoxazolyl, thiazolyl, imidazolyl, pyridazinyl, quinolinyl, quinazolinyl, benzothienyl, benzofuryl, benzimidazolyl, pyrazolyl, benzothiazolyl, benzoxazolyl, and any one of said heteroaryl groups in combination with $—CH_2$, $—CH_2—CH_2—$ or $—C(CH_3)$ and wherein each of the aromatic rings may be optionally substituted by one, two or three radicles selected from the group consisting of halogen, $C_{1-4}$ alkyl, $C_{1-4}$ alkoxy, $C_{1-4}$ haloalkyl, $C_{1-4}$ haloalkoxy, $C_{2-8}$ acyl, benzoyl, $C_{1-4}$ alkylthio, cyano, phenyl, phenoxy, nitro and $—C(CH_3)=N—O—C_{1-4}$ alkyl; and X is CH or nitrogen.

2. A compound according to claim 1 wherein the aromatic rings in $R_4$ are optionally substituted by one, two or three radicals selected from the group comprising halogen, $C_{1-4}$alkyl, $C_{1-4}$alkoxy, $C_{1-4}$haloalkyl, $C_{1-4}$haloalkoxy, $C_{1-4}$alkylthio, cyano, phenyl, phenoxy, nitro, or a group $—C(CH_3)=N—O—C_{1-4}$alkyl.

3. A compound according to claim 1, wherein $R_1$ is methyl, ethyl, or cyclopropyl.

4. A compound according to claim 1, wherein $R_2$ is methyl, or methoxy.

5. A compound according to claim 1, wherein the pyrazole ring is linked to the oxygen bridge in the 3- or 4-position.

6. A compound according to claim 1, wherein $R_4$ is chlorophenyl, dichlorophenyl, fluorophenyl, methyl-chlorophenyl, trifluoromethylphenyl, trifluoromethyl-chlorophenyl, difluoromethoxyphenyl, trifluoromethoxyphenyl, methylphenyl, or dimethylphenyl.

7. A compound according to claim 1, wherein $R_1$ and $R_2$ are methyl, $R_4$ is chlorophenyl, dichlorophenyl, fluorophenyl, methyl-chlorophenyl, trifluoromethylphenyl, trifluoromethyl-chlorophenyl, difluoromethoxyphenyl, trifluoromethoxyphenyl, methylphenyl, or dimethylphenyl.

8. A compound according to claim 7, wherein X is CH.

9. A compound according to claim 1, selected from the group comprising methyl 2-[2,4-dimethyl-6-(1-(3-trifluoromethylphenyl)-1H-pyrazol-3-yloxy)-pyrimidin-5-yl]-3-methoxyacrylate;

methyl 2-[2,4-dimethyl-6-(1-(3,5-dimethylphenyl)-1H-pyrazol-4-yloxy)-pyrimidin-5-yl]-3-methoxyacrylate;

methyl 2-[2,4-dimethyl-6-(1-(5-chloro-2-methylphenyl)-1H-pyrazol-3-yloxy)-pyrimidin-5-yl]-3-methoxyacrylate; and methyl 2-[2-methyl-4-methoxy-6-(1-(5-chloro-2-methylphenyl)-1H-pyrazol-3-yloxy)-pyrimidin-5-yl]-3-methoxyacrylate.

10. Method of combatting phytopathogenic fungi comprising applying to the fungi or their habitat a fungicidally effective amount of a compound of formula I according to claim 1.

11. Fungicidal composition comprising a compound of formula I stated in claim 1 and a agriculturally acceptable diluent.

12. A compound of formula II

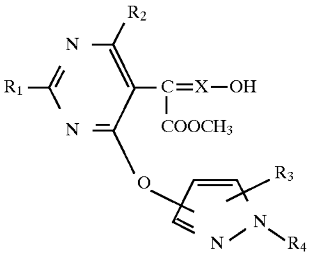

(II)

wherein $R_1$ is hydrogen, $C_{1-4}$alkyl, $C_{1-4}$ alkoxy, $C_{3-6}$ cycloalkyl, $C_{1-4}$ alkylthio, or di- $C_{1-4}$ alkylamino, $R_2$ is hydrogen, $C_{1-4}$ alkyl, $C_{1-4}$ alkoxy, $C_{1-4}$ alkylthio, or di- $C_{1-4}$ alkylamino, $R_3$ is hydrogen or methyl, $R_4$ is phenyl, naphthyl, benzyl, phenyethyl, phenylpropyl, 1-phenylethyl, or a heteroaryl selected from the group consisting of pyridyl, pyrimidinyl, thienyl, oxazolyl, oxadiazolyl, triazolyl, thiadiazolyl, furyl, isoxazolyl, thiazolyl, imidazolyl, pyridazinyl, quinolinyl, quinazolinyl, benzothienyl, benzofuryl, benzimidazolyl, pyrazolyl, benzothiazolyl, benzoxazolyl, and any one of said heteroaryl groups in combination with $—CH_2$, $—CH_2—CH_2—$ or $—C(CH_3)$ and wherein each of the aromatic rings may be optionally substituted by one, two or three radicles selected from the group consisting of halogen, $C_{1-4}$ alkyl, $C_{1-4}$ alkoxy, $C_{1-4}$ haloalkyl, $C_{1-4}$ haloalkoxy, $C_{2-8}$ acyl, benzoyl, $C_{1-4}$ alkylthio, cyano, phenyl, phenoxy, nitro and $—C(CH_3)═N—O—C_{1-4}$ alkyl; and X is CH or nitrogen.

* * * * *